US012310571B2

(12) United States Patent
Martinelli et al.

(10) Patent No.: US 12,310,571 B2
(45) Date of Patent: May 27, 2025

(54) SURGICAL ACCESS SYSTEM AND RELATED METHODS

(71) Applicant: NuVasive, Inc., San Diego, CA (US)

(72) Inventors: Scot Martinelli, San Diego, CA (US);
Jared Arambula, San Diego, CA (US);
Eric Finley, San Diego, CA (US);
Patrick Miles, San Diego, CA (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 18/337,191

(22) Filed: Jun. 19, 2023

(65) Prior Publication Data

US 2023/0404564 A1    Dec. 21, 2023

Related U.S. Application Data

(63) Continuation of application No. 17/162,292, filed on Jan. 29, 2021, now Pat. No. 11,723,644, which is a
(Continued)

(51) Int. Cl.
*A61B 17/02* (2006.01)
*A61B 5/00* (2006.01)
(Continued)

(52) U.S. Cl.
CPC ............ *A61B 17/025* (2013.01); *A61B 5/389* (2021.01); *A61B 5/395* (2021.01); *A61B 5/742* (2013.01); *A61B 17/02* (2013.01); *A61B 17/0206* (2013.01); *A61B 17/0218* (2013.01); *A61B 17/848* (2013.01); *A61F 2/4455* (2013.01); *A61F 2/4611* (2013.01); *A61N 1/0551* (2013.01); *A61N 1/36017* (2013.01);
*A61B 2017/00022* (2013.01); *A61B 2017/00199* (2013.01); *A61B 2017/00407* (2013.01); *A61B 2017/0256* (2013.01);
(Continued)

(58) Field of Classification Search
CPC .................. A61B 17/02; A61B 17/025; A61B 2017/0256; A61B 2017/0262
USPC .................................................. 600/201–246
See application file for complete search history.

(56) References Cited

U.S. PATENT DOCUMENTS 5,931,777 A * 8/1999 Sava ...................... A61B 17/02
                                                    600/210
5,944,658 A * 8/1999 Koros ................. A61B 17/7077
                                                    600/231

(Continued)

FOREIGN PATENT DOCUMENTS

WO    WO-03026482 A2 *  4/2003  ............... A61B 1/32

*Primary Examiner* — Matthew J Lawson

(57) ABSTRACT

A surgical access system including a tissue distraction assembly 40 and a tissue retraction assembly 10, both of which may be equipped with one or more electrodes 23 for use in detecting the existence of (and optionally the distance and/or direction to) neural structures before, during, and after the establishment of an operative corridor 15 to a surgical target site. The tissue retraction assembly 10 has a plurality of blades 12, 16, 18 which may be introduced while in a closed configuration, after which point they may be opened to create an operation corridor 15 to the surgical target site, including pivoting at least one blade 12, 16, 18 to expand the operative corridor 15 adjacent to the operative site.

12 Claims, 49 Drawing Sheets

Related U.S. Application Data continuation of application No. 16/400,972, filed on May 1, 2019, now Pat. No. 11,308,589, which is a continuation of application No. 15/484,871, filed on Apr. 11, 2017, now abandoned, which is a continuation of application No. 11/665,039, filed as application No. PCT/US2005/036454 on Oct. 11, 2005, now Pat. No. 9,622,732.

(60) Provisional application No. 60/720,710, filed on Sep. 26, 2005, provisional application No. 60/617,498, filed on Oct. 8, 2004.

(51) Int. Cl.
*A61B 5/389* (2021.01)
*A61B 5/395* (2021.01)
*A61B 17/84* (2006.01)
*A61F 2/44* (2006.01)
*A61F 2/46* (2006.01)
*A61N 1/05* (2006.01)
*A61N 1/36* (2006.01)
*A61B 17/00* (2006.01)

(52) U.S. Cl.
CPC ... *A61B 2017/0262* (2013.01); *A61B 2505/05* (2013.01); *A61F 2002/4619* (2013.01); *A61N 1/36003* (2013.01)

(56) References Cited

U.S. PATENT DOCUMENTS

| | | | | |
|---|---|---|---|---|
| 5,967,973 | A * | 10/1999 | Sherts | A61M 1/77 600/233 |
| 6,196,969 | B1 * | 3/2001 | Bester | A61B 17/0206 600/219 |
| 6,869,398 | B2 * | 3/2005 | Obenchain | A61B 1/32 600/210 |
| 7,513,869 | B2 * | 4/2009 | Branch | A61B 17/3439 600/233 |
| 7,976,463 | B2 * | 7/2011 | Dewey | A61B 17/3439 600/233 |
| 8,353,826 | B2 * | 1/2013 | Weiman | A61B 17/0206 600/231 |
| 2002/0111538 | A1 * | 8/2002 | Wright | A61B 17/0293 600/233 |
| 2005/0004593 | A1 * | 1/2005 | Simonson | A61B 17/025 606/191 |
| 2005/0080320 | A1 * | 4/2005 | Lee | A61B 17/0293 600/214 |
| 2005/0215866 | A1 * | 9/2005 | Kim | A61B 17/0293 600/233 |
| 2007/0198062 | A1 * | 8/2007 | Miles | A61B 1/32 607/2 |

* cited by examiner

SURGICAL ACCESS SYSTEM AND RELATED METHODS

CROSS-REFERENCES TO RELATED APPLICATIONS

The present application is a continuation of U.S. patent application Ser. No. 16/400,978, filed May 1, 2019, which is a continuation of U.S. patent application Ser. No. 15/484,871, filed Apr. 11, 2017, which is a continuation of U.S. patent application Ser. No. 11/665,039, filed Apr. 9, 2007, which is a U.S. national phase under 35 U.S.C. 371 of international application PCT/US2005/036454, filed Oct. 11, 2005. International patent application PCT/US2005/036454 claims the benefit of priority from U.S. provisional patent application 60/617,498, filed Oct. 8, 2004, and U.S. provisional patent application 60/720,710, filed Sep. 26, 2005. The entire contents of these priority applications are hereby expressly incorporated by reference into this disclosure as if set forth fully herein.

BACKGROUND OF THE INVENTION

I. Field of the Invention

The present invention relates generally to systems and methods for performing surgical procedures and, more particularly, for accessing a surgical target site in order to perform surgical procedures.

II. Discussion of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (e.g. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY OF THE INVENTION

The present invention accomplishes this goal by providing a novel access system and related methods which involve detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present invention is suitable for use in any number of additional surgical procedures wherein tissue having significant neural structures must be passed through (or near) in order to establish an operative corridor. It is also expressly noted that, although shown and described herein largely within the context of lateral surgery in the lumbar spine, the access system of the present invention may be employed in any number of other spine surgery access approaches, including but not limited to posterior, postero-lateral, anterior, and antero-lateral access, and may be employed in the lumbar, thoracic and/or cervical spine, all without departing from the present invention.

According to one broad aspect of the present invention, the access system comprises a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire and one or more dilators (e.g., sequentially dilating cannulae) for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another (simultaneously or sequentially) to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that doesn't impinge upon the region of the exiting nerve roots. In one optional aspect of the present invention, the cephalad-most and/or caudal-most blades may pivot or rotate outward from a central axis of insertion, such that the operative corridor may be further expanded. In a further optional aspect of the present invention, the retractor may include a locking element to maintain the blades in an initial alignment during insertion, and a variable-stop mechanism to allow the user to control the degree of expansion of the operative corridor. A blade expander tool may be provided to facilitate manual pivoting of the retractor blades.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior retractor blade is equipped with such a rigid shim element. In an optional aspect, this shim element may be advanced into the disc space after the posterior retractor blade is positioned, but before the retractor is opened into the folly retracted position. The rigid shim element is preferably oriented within the disc space such that is distracts the adjacent vertebral bodies, which serves to restore disc height. It also preferably advances a sufficient distance within the disc space (preferably past the midline), which advantageously forms a protective barrier that prevents the migration of tissue (such as nerve roots) into the operative field and the inadvertent advancement of instruments outside the operative field. In an optional embodiment, the caudal-most and/or cephalad-most blades may be fitted with any number of retractor extenders for extending (laterally or length-wise) the blades, which advantageously forms a protective barrier that prevents the migration of tissue (such as muscle and soft tissue) into the operative field and the inadvertent advancement of instruments outside the operative field.

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, coupling one or more light sources to the retractor blades such that the terminal ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
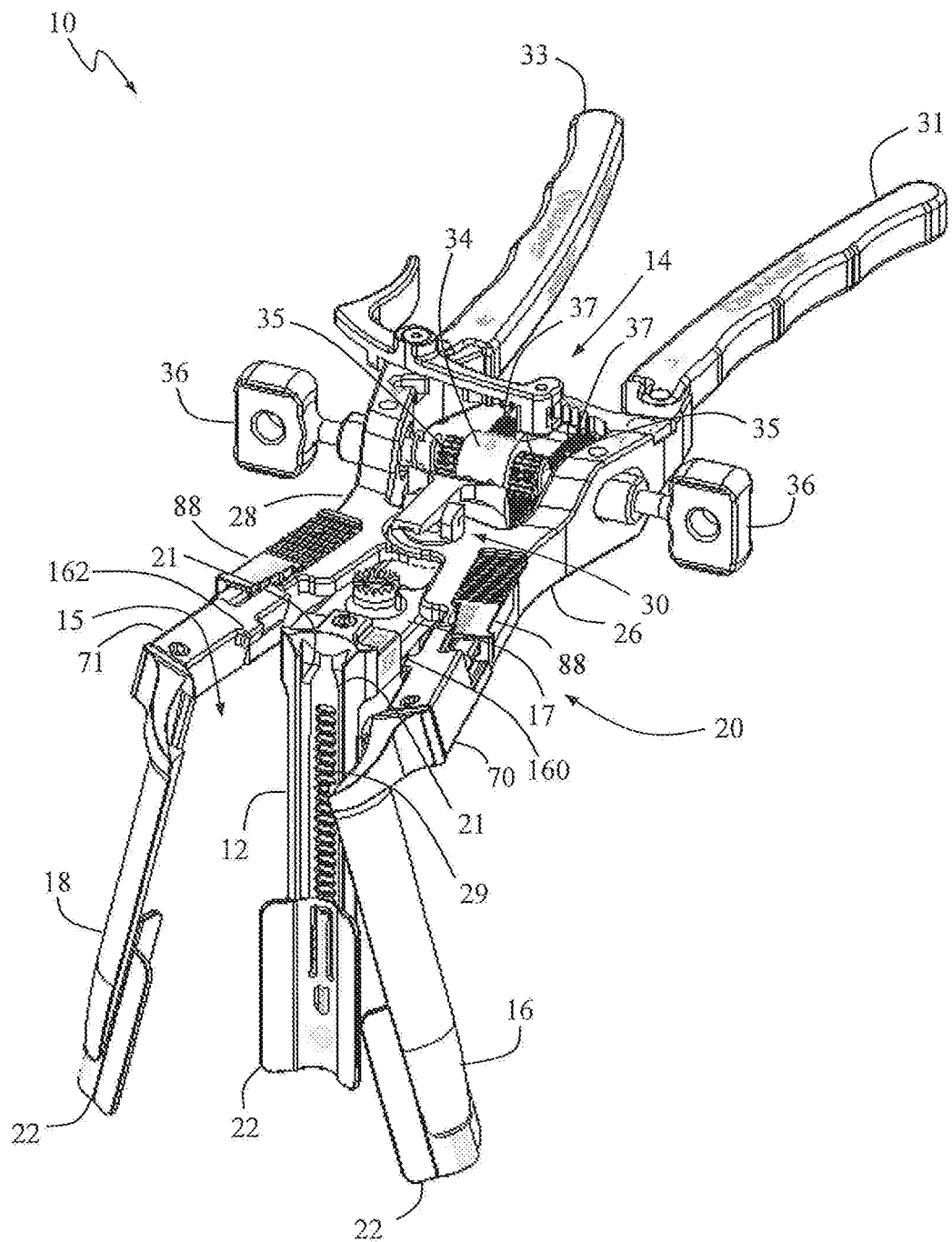
FIG. 1 is a perspective view of a tissue retraction assembly forming part of a surgical access system according to the present invention, shown in a fully retracted or "open" position.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. It is also expressly noted that, although shown and described herein largely within the context of lateral surgery in the lumbar spine, the access system of the present invention may be employed in any number of other spine surgery access approaches, including but not limited to posterior, postero-lateral, anterior, and antero-lateral access, and may be employed in the lumbar, thoracic and/or cervical spine, all without departing from the present invention. The surgical access system disclosed herein boasts-a variety of inventive features and components that warrant patent protection, both individually and in combination.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in the above referenced Neuro-Vision PCT Applications. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a plurality of sequentially dilating cannulae) is employed to distract the tissues extending between the skin of the patient and a given surgical target site (preferably along the posterior region of the target intervertebral disc). Once distracted, the resulting void or distracted region within the patient is of sufficient size to accommodate a tissue retraction assembly of the present invention. More specifically, the tissue retraction assembly (comprising a plurality of retractor blades extending from a handle assembly) may be advanced relative to the secondary distraction assembly such that the retractor blades, in a first, closed position, are advanced over the exterior of the secondary distraction assembly. At that point, the handle assembly may be operated to move the retractor blades into a second, open or "retracted" position to create an operative corridor to the surgical target site.

According to one aspect of the invention, following (or before) this retraction, a posterior shim element (which is preferably slidably engaged with the posterior retractor blade) may be advanced such that a distal shim extension in positioned within the posterior region of the disc space. If done before retraction, this helps ensure that the posterior retractor blade will not move posteriorly during the retraction process, even though the other retractor blades (e.g. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (e.g. nerves, vasculature, etc. . . . ) into or out of the operative corridor. Optionally, the cephalad-most and/or caudal-most retractor blades may be pivoted in an outward direction to further expand the operative corridor. Once the operative corridor is established, any of a variety of surgical instruments, devices, or implants may be passed through and/or manipulated within the operative corridor depending upon the given surgical procedure.

Figure 2:
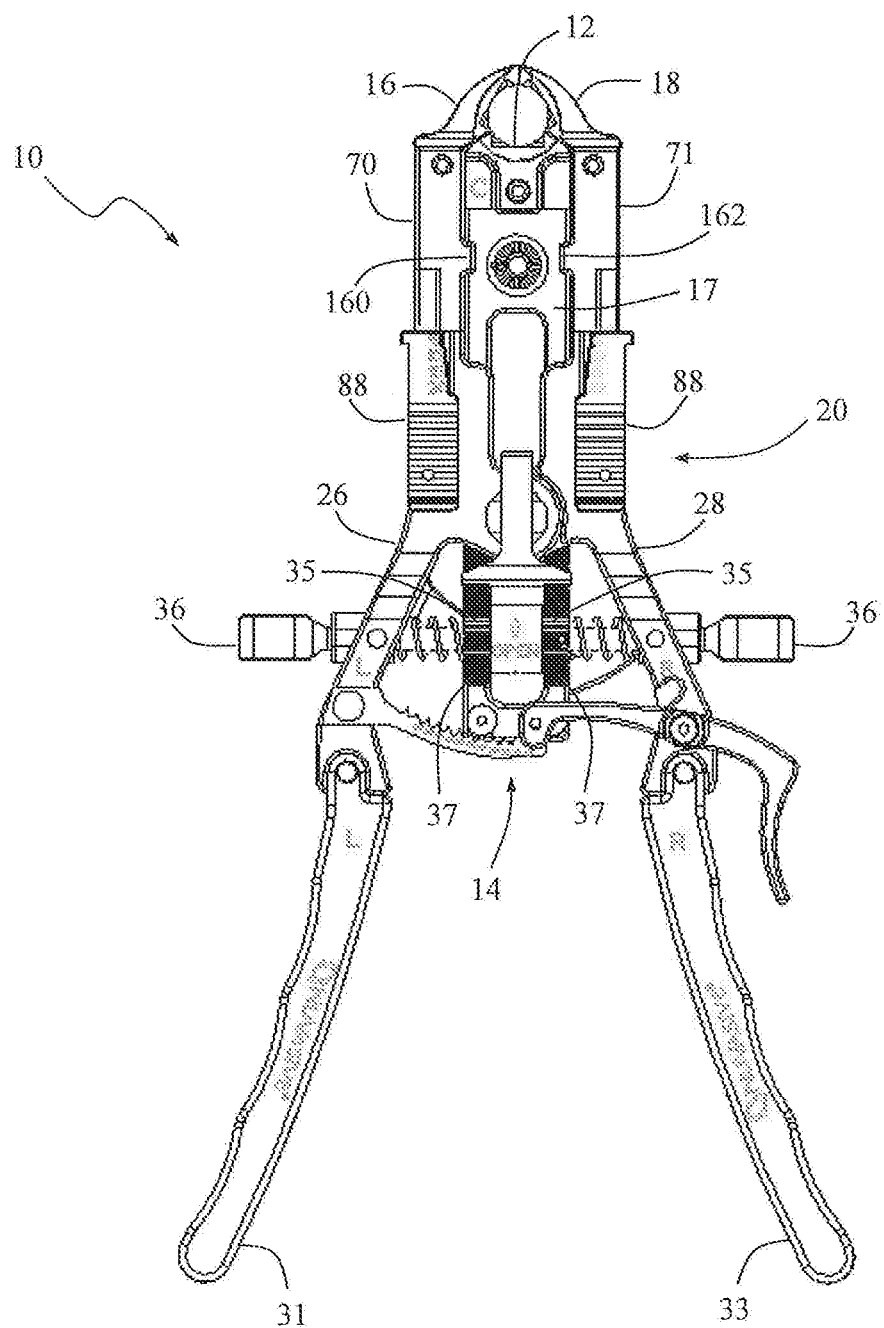
FIGS. 2-3 are top and perspective views, respectively, of the tissue retraction assembly of FIG. 1 shown in a closed position according to the present invention.
Figure 3:
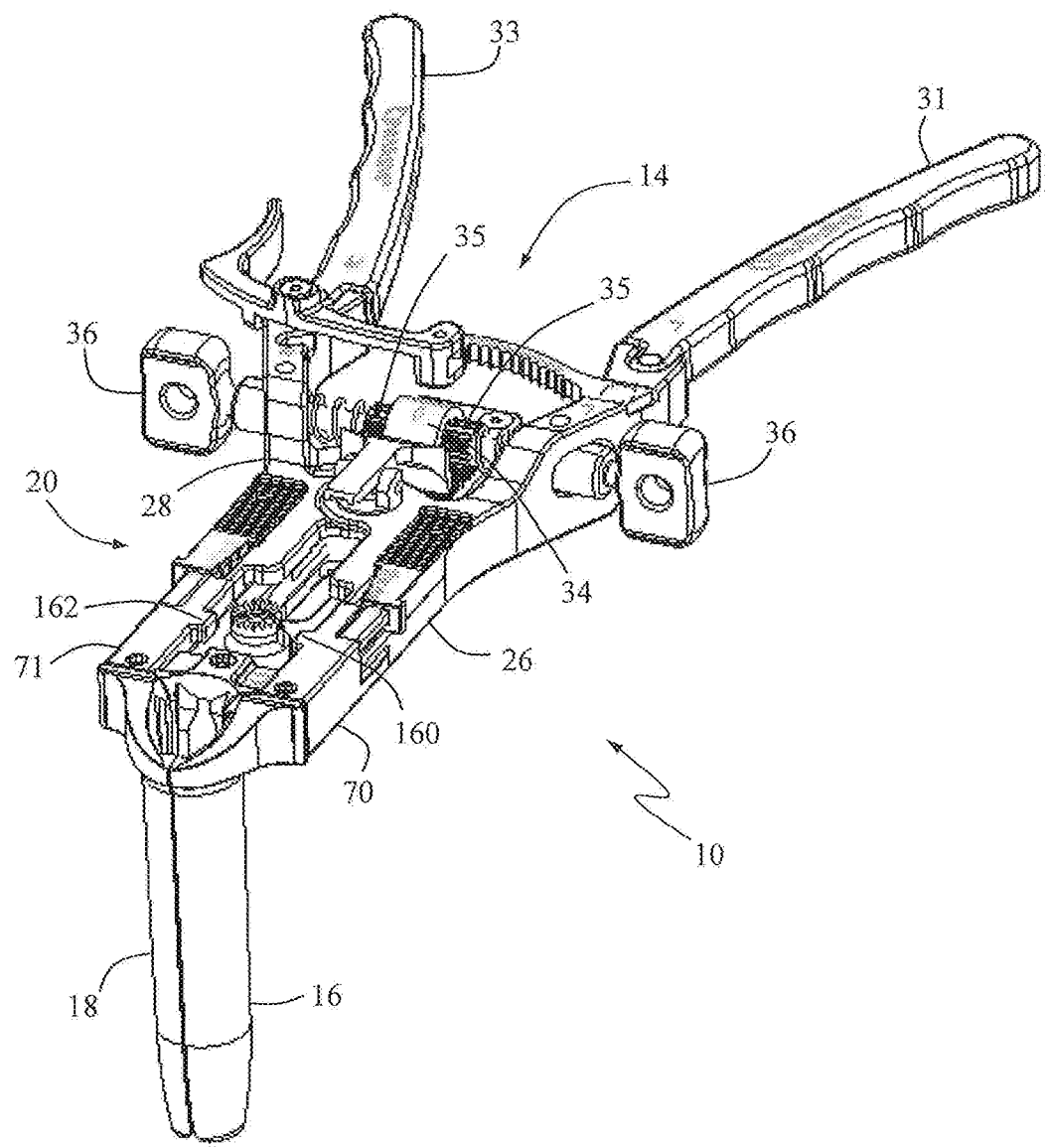
Figure 4:
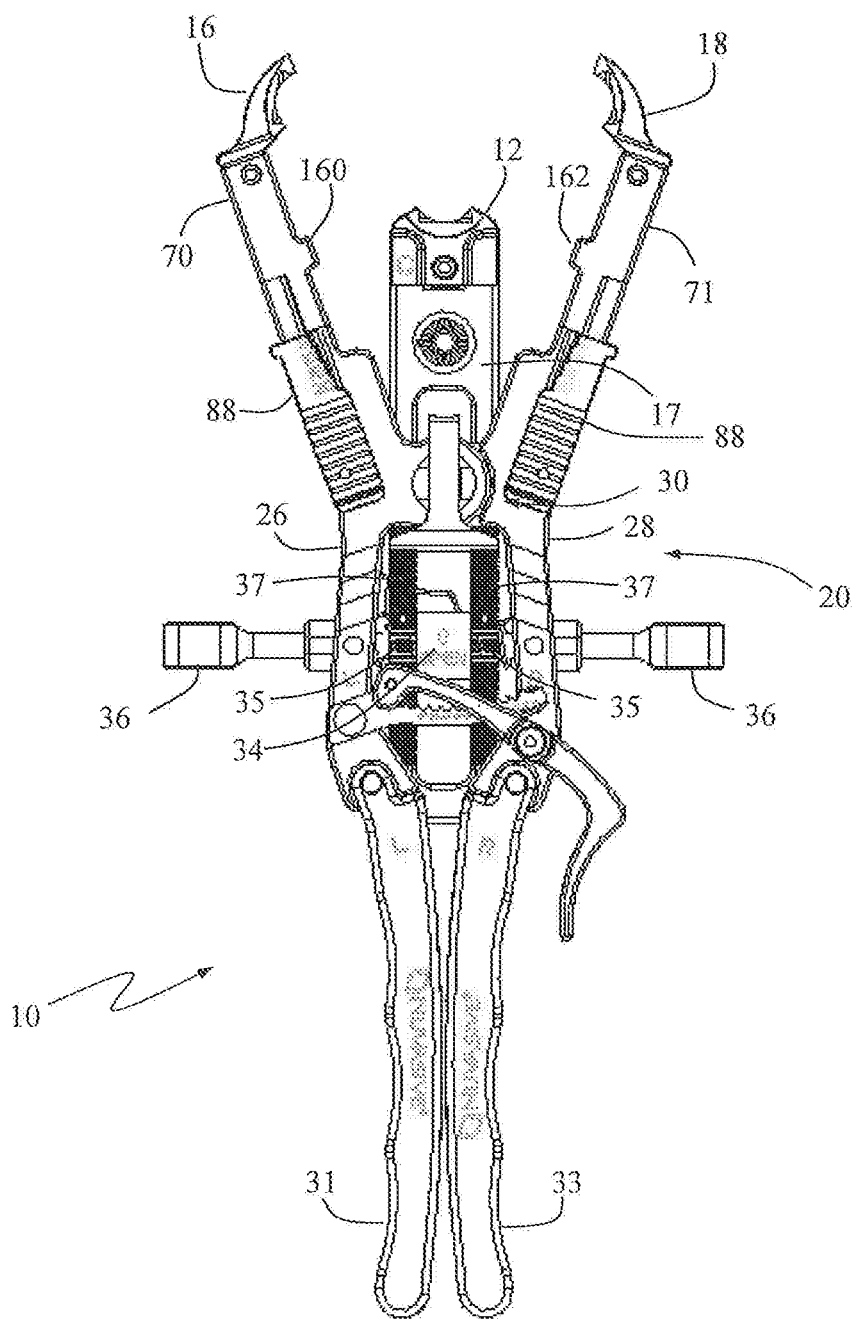
FIGS. 4-5 are top and perspective views, respectively, of the tissue retraction assembly of FIG. 1 in an open position.
Figure 5:
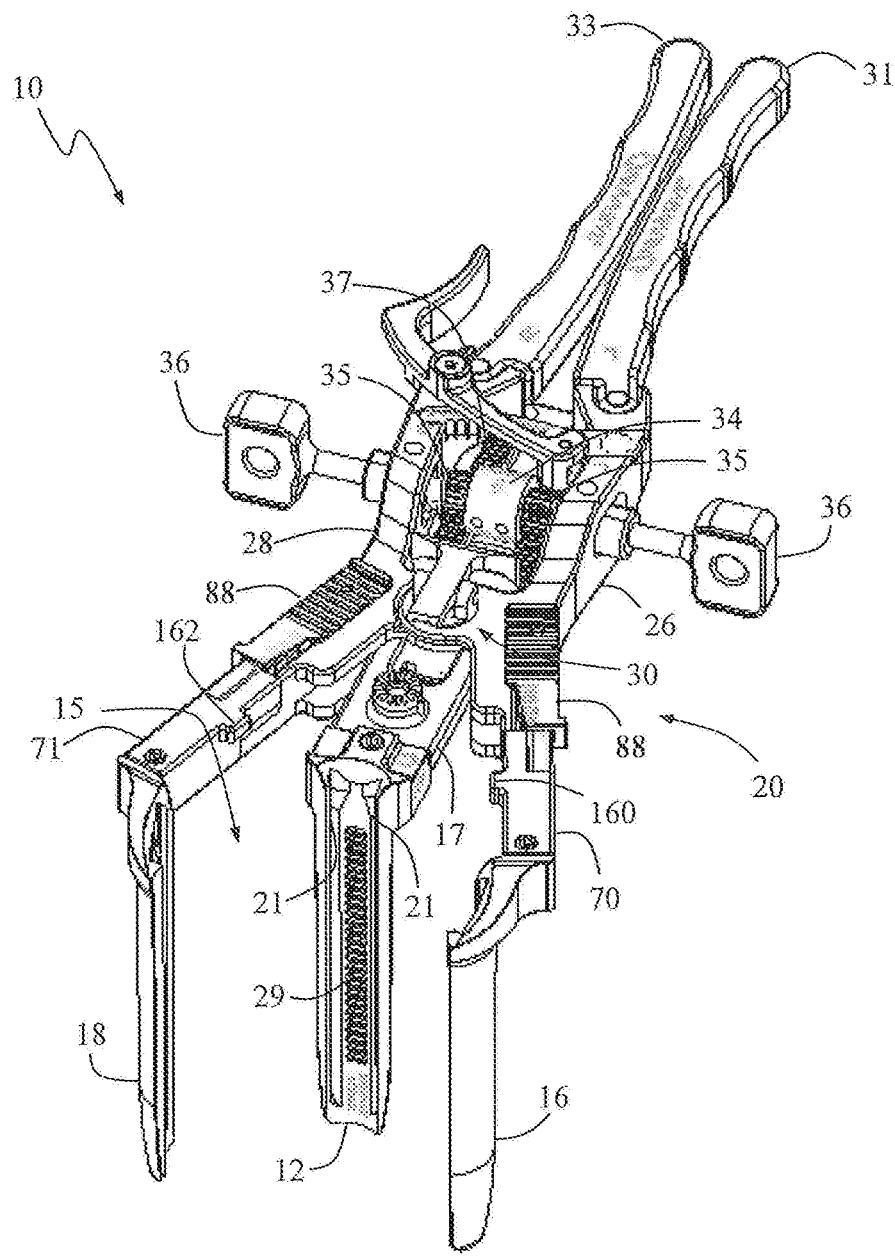

FIGS. 1-5 illustrate a tissue retraction assembly 10 forming part of a surgical access system according to the present invention, including a plurality of retractor blades extending from a handle assembly 20. By way of example only, the handle assembly 20 is provided with a first retractor blade 12, a second retractor blade 16, and a third retractor blade 18. FIG. 1 illustrates the retractor assembly 10 in a fully retracted or "open" configuration, with the retractor blades 12, 16, 18 positioned a distance from one another so as to form an operative corridor 15 therebetween which extends to a surgical target site (e.g. an annulus of an intervertebral disc). In an important aspect of the present invention, the blades 16, 18 are capable of being pivoted or rotated relative to the handle 10, as best appreciated with combined reference to FIGS. 1 and 4-5. FIGS. 2-3 show the retractor assembly 10 in an initial "closed" configuration, with the retractor blades 12, 16, 18 in a generally abutting relation to one another. Although shown and described below with regard to the three-bladed configuration, it is to be readily appreciated that the number of retractor blades may be increased or decreased without departing from the scope of the present invention. Moreover, although described and shown herein with reference to a generally lateral approach to a spinal surgical target site (with the first blade 12 being the "posterior" blade, the second blade 16 being the "cephalad-most" blade, and the third blade 18 being the "caudal-most" blade), it will be appreciated that the retractor assembly 10 of the present invention may find use in any number of different surgical approaches, including generally posterior, generally postero-lateral, generally anterior and generally antero-lateral.

The retractor blades 12, 16, 18 may be composed of any material suitable for introduction into the human body, including but not limited to aluminum, titanium, and/or clear polycarbonate, that would ensure rigidity during tissue distraction. The retractor blades 12, 16, 18 may be optionally coated with a carbon fiber reinforced coating to increase strength and durability. The blades 12, 16, 18 may be optionally constructed from partially or wholly radiolucent materials (e.g. aluminum, PEEK, carbon-fiber, and titanium) to improve the visibility of the surgeon during imaging (e.g. radiographic, MRI, CT, fluoroscope, etc. . . . ). The retractor blades 12, 14, 18 may also be composed of a material that would destruct when autoclaved (such as polymer containing a portion of glass particles), which may be advantageous in preventing the unauthorized re-use of the blades 12, 16, 18 (which would be provided to the user in a sterile state). The retractor blades 12, 16, 18 may be provided in any number of suitable lengths, depending upon the anatomical environment and surgical approach, such as (by way of example only) the range from 20 mm to 150 mm. Based on this range of sizes, the tissue retraction assembly 10 of the present invention is extremely versatile and may be employed in any of a variety of desired surgical approaches, including but not limited to lateral, posterior, postero-lateral, anterior, and antero-lateral, by simply selecting the desired size retractor blades 12, 16, 18 and attaching them to the handle assembly 20 as will be described herein.

Figure 6:
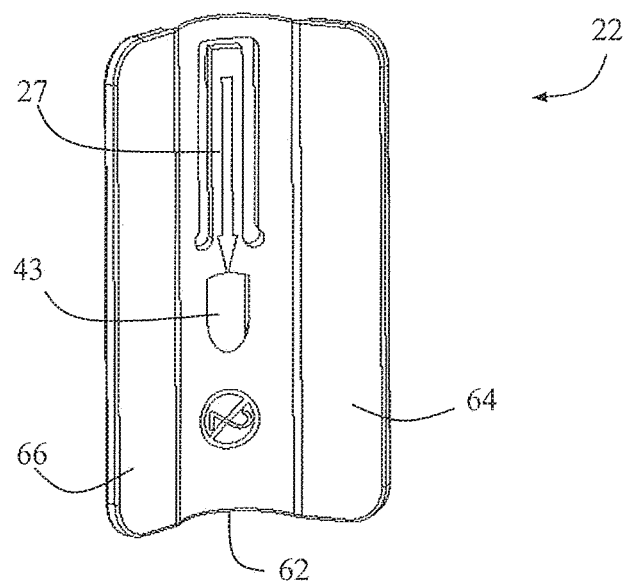
FIGS. 6-7 are perspective views illustrating the front and back of a wide retractor extender for use with any one of the retractor blades according to the retractor of the present invention.
Figure 7:
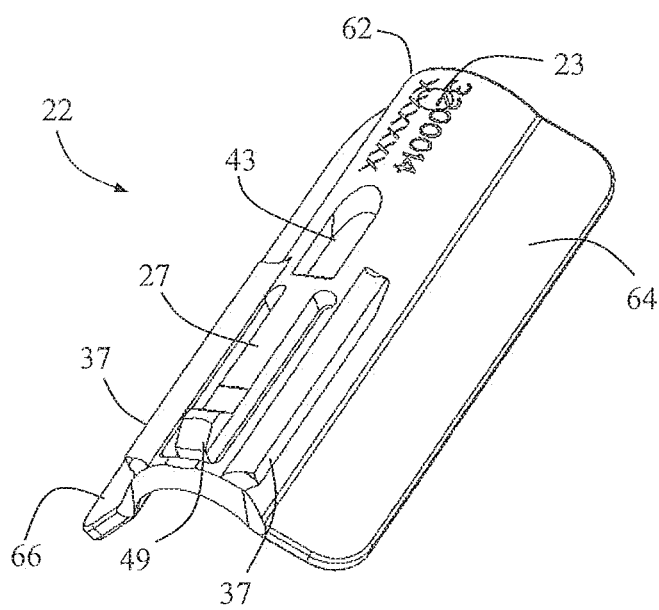
Figure 8:
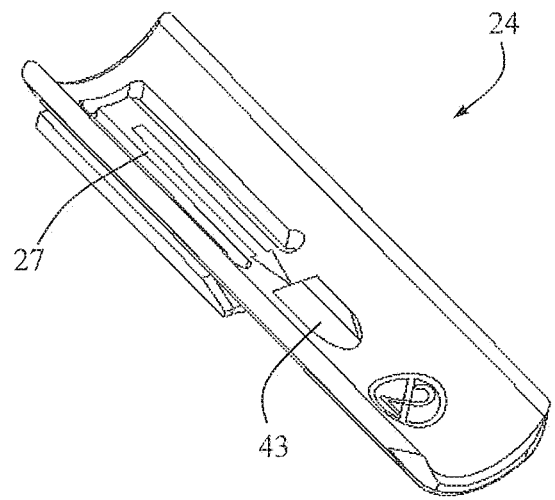
FIGS. 8-9 are perspective views illustrating the front and back of a narrow retractor extender for use with one of the retractor blades according to the retractor of the present invention.
Figure 9:
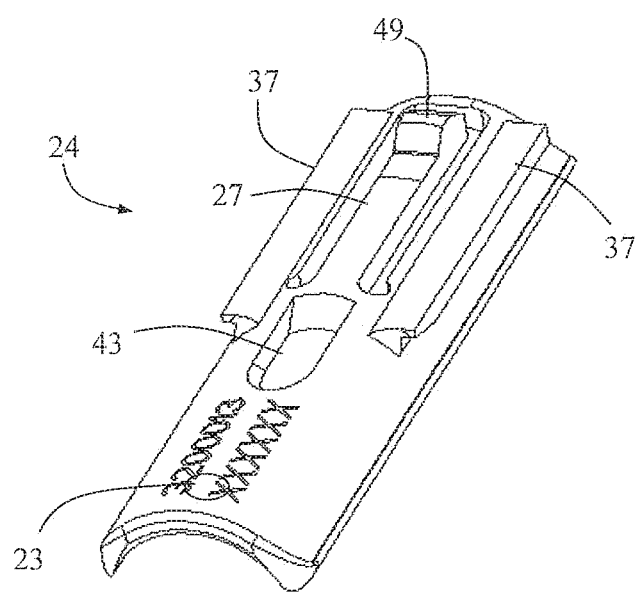
Figure 10:
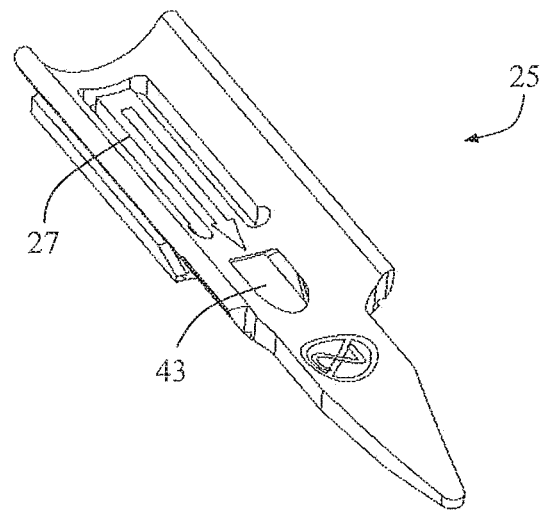
FIGS. 10-11 are perspective views illustrating the front and back of a shim element for use with a posterior retractor blade of the retractor according to the retractor of the present invention.
Figure 11:
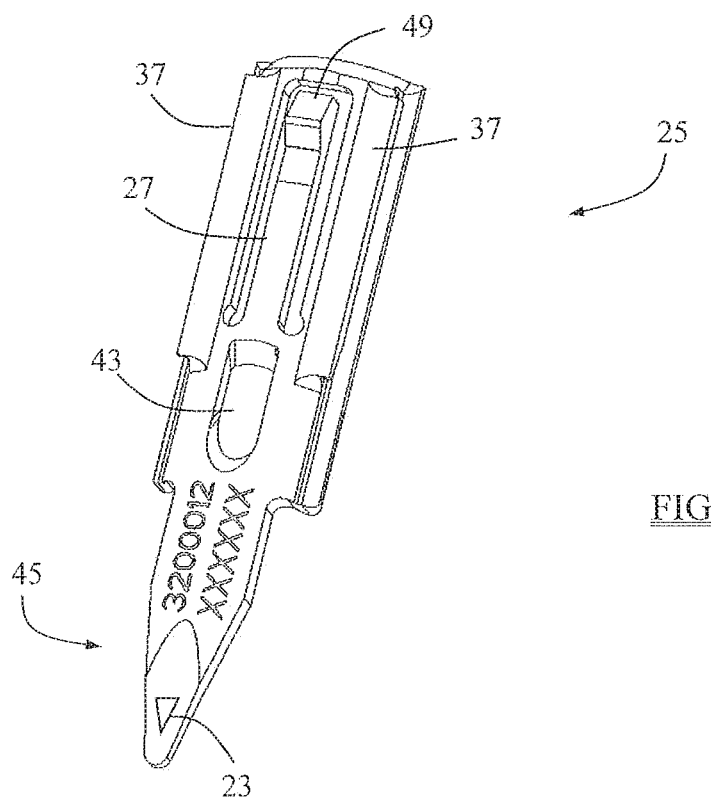
Figure 12:
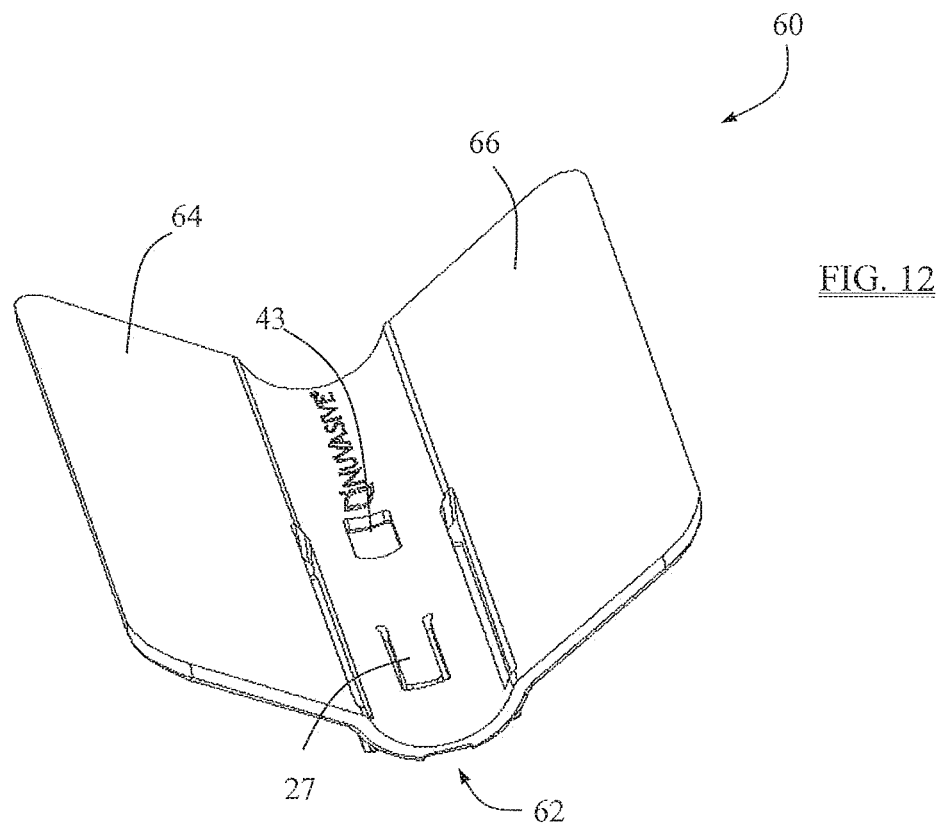
FIGS. 12-13 are perspective views of the front and back, respectively, of a shim element according to one embodiment of the present invention.
Figure 13:
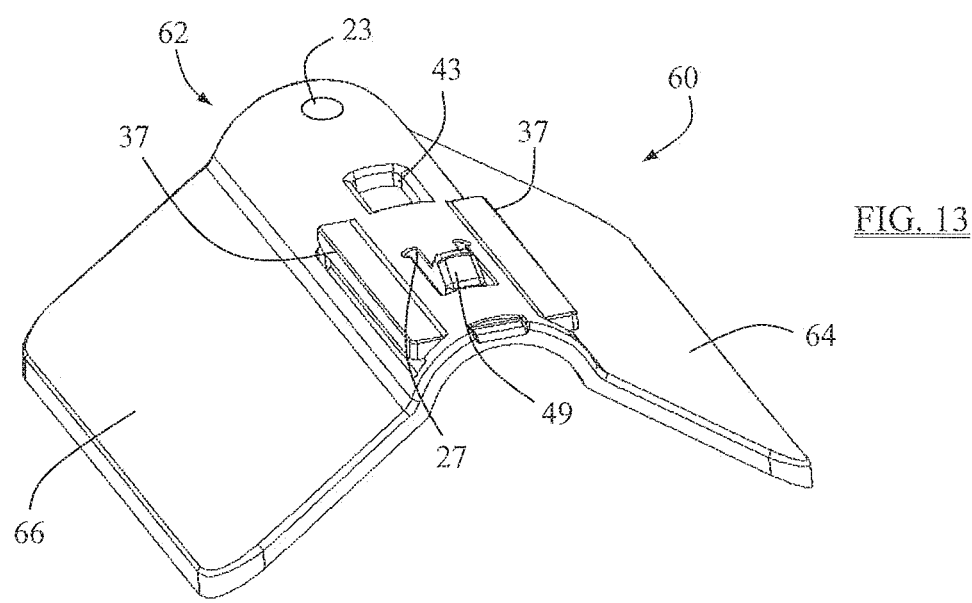
Figure 14:
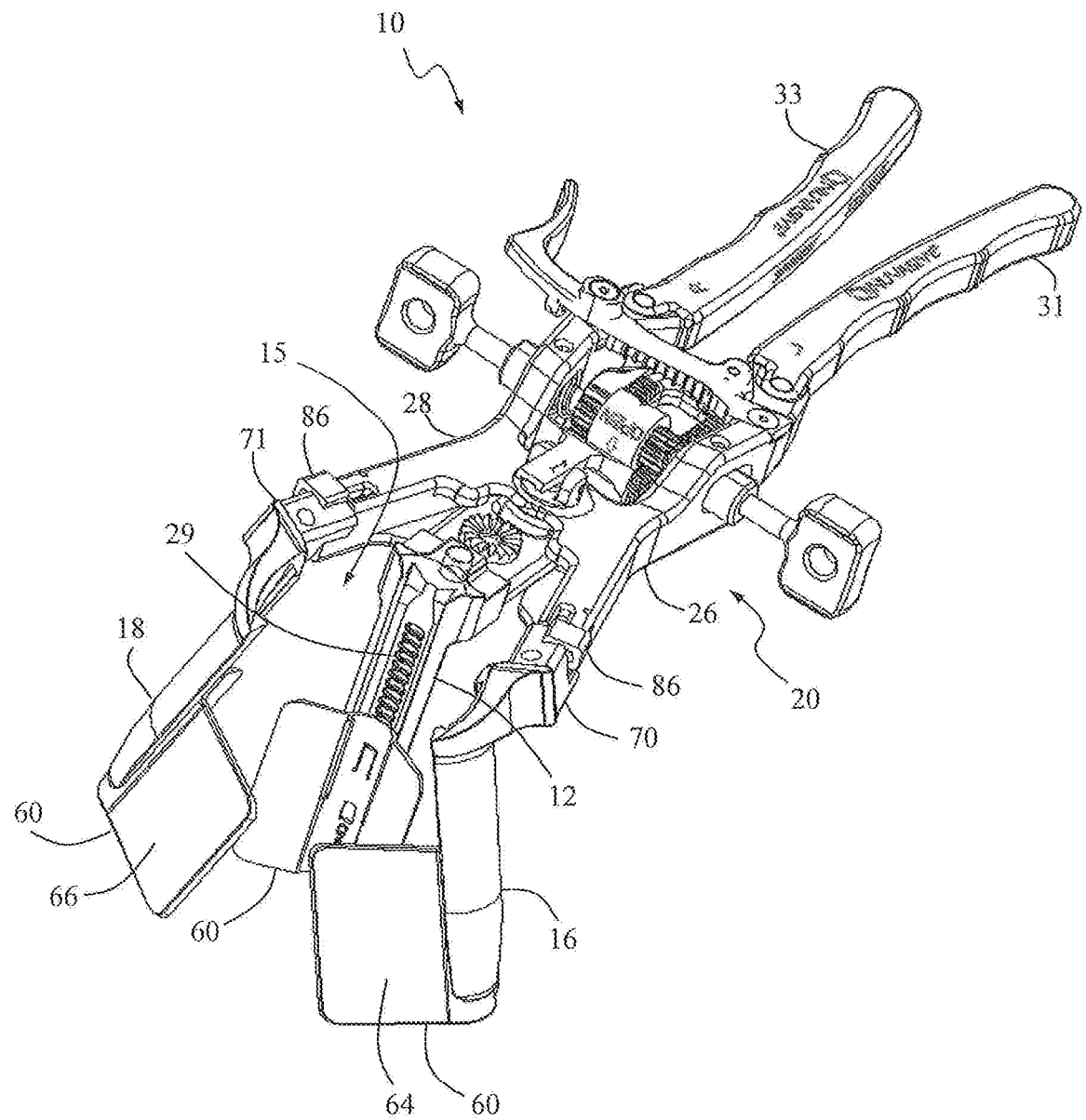
FIGS. 14-15 are perspective and top views, respectively, of a tissue retraction assembly of according to one embodiment of the present invention, shown in an open position with a shim and/or retractor extender installed on each retractor blade.
Figure 15:
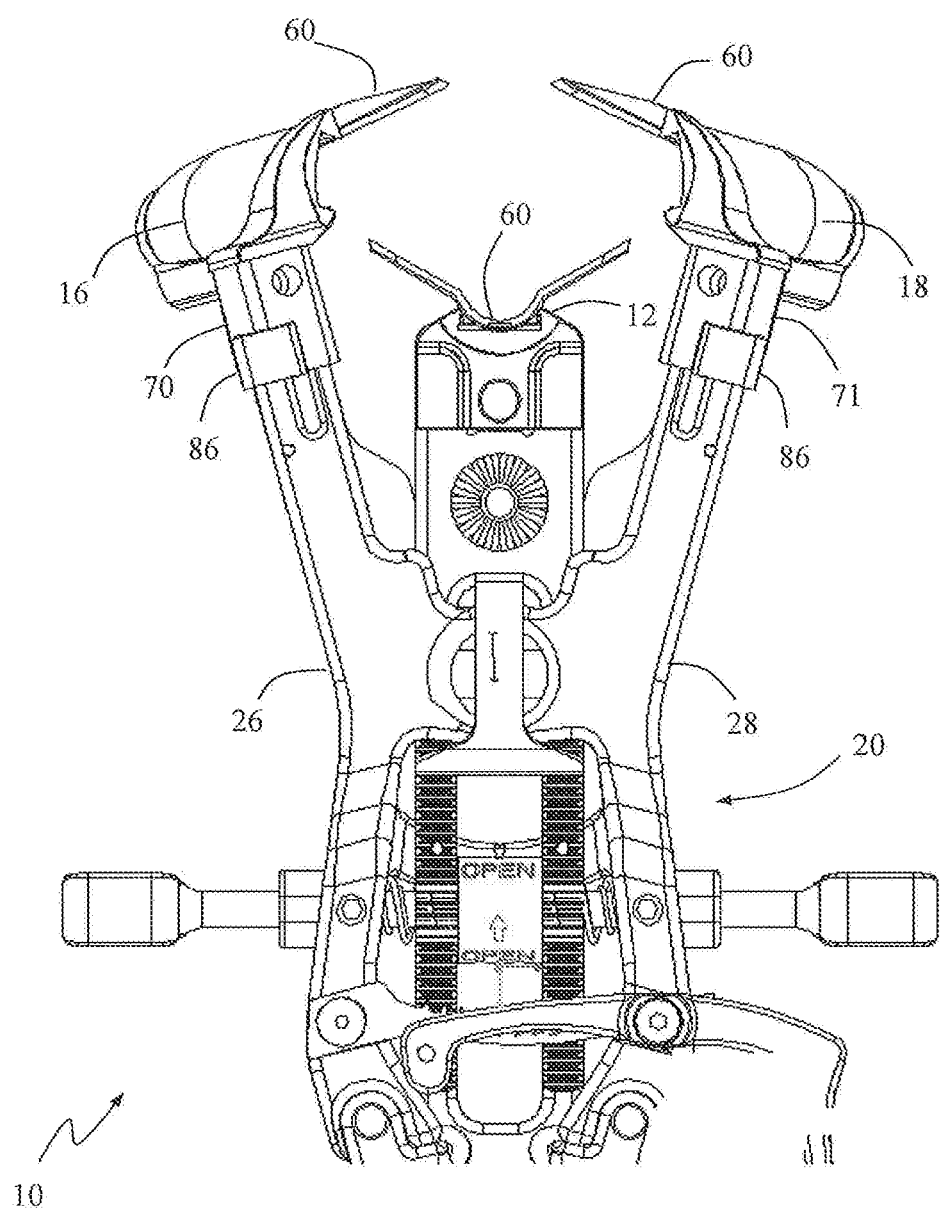

The retractor blades 12, 16, 18 may be equipped with various additional features or components. By way of example only, one or more of the retractor blades 12, 16, 18 may be equipped with a retractor extender, such as a wide retractor extender 22 as shown in FIGS. 6-7, a narrow retractor extender 24 as shown in FIGS. 8-9 and/or an extra wide retractor extender 60 as shown in FIGS. 12-13. The retractor extenders 22, 24, 60 extend from the retractor blades 12, 16, 18 (as shown in FIGS. 14-15, by way of example, with reference to retractor extender 60) to form a protective barrier to prevent the ingress or egress of instruments or biological structures (e.g. nerves, vasculature, etc. . . . ) into or out of the operative corridor 15. Depending upon the anatomical setting and surgical approach, one or more of the retractor blades 12, 16, 18 may be equipped with a shim element 25 as shown in FIGS. 10-11. Shim element 25 has a distal tapered region 45 which may be advanced into tissue (e.g. bone, soft tissue, etc. . . . ) for the purpose of anchoring the blades 12, 16, 18 and/or advanced into the disc space to distract the adjacent vertebral bodies (thereby restoring disc height). In similar fashion to the retractor extenders 22, 24, 60, the shim element 25 also forms a protective barrier to prevent the ingress or egress of instruments or biological structures (e.g. nerves, vasculature, etc. . . . ) into or out of the operative corridor 15.

Retractor extenders 22, 24, 60 and/or shim element 25 may be made out any material suitable for use in the human body, including but not limited to biologically compatible plastic and/or metal, preferably partially or wholly radiolucent in nature material (such as aluminum, PEEK, carbon-fibers and titanium). Construction from plastic or thin metal provides the additional benefit of allowing the shim 25 and/or retractor extenders 22, 24, 60 to be collapsed into a compressed or low profile configuration at the skin level as the element is inserted, and then expanded once it is below skin level and within the operative corridor 15. Retractor extenders 22, 24, 60 may have symmetric narrow configurations (FIGS. 8-9) and/or broad configurations (FIGS. 6-7 and 12-13) and/or an asymmetric configuration of narrow and broad elements (FIGS. 14-15). For example, any or all of the retractor extenders 22, 24, 60 may be provided with a lateral section 64 of the type shown in FIGS. 6-7, a narrow configuration (without lateral sections 64, 66) of the type shown in FIGS. 8-9, and/or a lateral section 66 of the type shown in FIGS. 12-13, all without departing from the scope of the present invention. The retractor extenders 22, 24, 60 and/or the shim element 25 may be composed of a material that would destruct when autoclaved (such as polymer containing a portion of glass particles), which may be advantageous in preventing the unauthorized re-use of the retractor extenders 22, 24, 60 and/or the shim element 25 (which would be provided to the user in a sterile state). Slits may also be provided on the shim 25 to improve flexibility. The retractor extenders 22, 24, 60 and/or the shim element 25 may have a parabolic concave curvature in addition to the configuration shown by way of example only in FIGS. 12-13.

Each of the retractor extenders 22, 24, 60 and/or the shim element 25 may be equipped with a mechanism to selectively and releasably engage with the respective retractor blades 12, 16, 18. By way of example only, this may be accomplished by configuring the retractor extenders 22, 24, 60 and/or the shim element 25 with a tab element 27 capable of engaging with corresponding ratchet-like grooves (shown at 29 in FIG. 1) along the inner-facing surfaces of the retractor blades 12, 16, 18. Each of the retractor extenders 22, 24, 60 and/or the shim element 25 is provided with a pair of engagement elements 37 having, by way of example only, a generally dove-tailed cross-sectional shape. The engagement elements 37 are dimensioned to engage with receiving portions 21 on the respective retractor blades 12, 16, 18. In a preferred embodiment, each of the retractor extenders 22, 24, 60 and/or the shim element 25 may be provided with an elongate slot 43 for engagement with an insertion tool 140 of the type shown in FIGS. 34-37 (as will be described in greater detail below). Each tab member 27 is also equipped with an enlarged tooth element 49 which engages within corresponding grooves 29 provided along the inner surface of the retractor blades 12, 16, 18. On the wide and extra wide retractor extenders 22, 60, respectively, each includes a center portion 62 flanked by a pair of lateral sections 64, 66, which effectively increase the width of the retractor blades 12, 16, 18.

According to the present invention, any or all of the retractor blades 12, 16, 18, the retractor extenders 22, 24, 60, and/or the shim element 25 may be provided with one or more electrodes 23 (preferably at or near their distal regions) equipped for use with a nerve surveillance system, such as, by way of example, the type shown and described in the NeuroVision PCT Applications. Such a nerve surveillance system is capable of detecting the existence of (and optionally the distance and/or direction to) neural structures during the retraction of tissue by detecting the presence of nerves by applying a stimulation signal to electrodes 23 and monitoring the evoked EMG signals from the myotomes associated with the nerves in the vicinity of the retraction system 10 of the present invention. In so doing, the system as a whole (including the surgical retraction system 10 of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

With reference to FIGS. 1-5, the handle assembly 20 may be coupled to any number of mechanisms for rigidly registering the handle assembly 20 in fixed relation to the operative site, such as through the use of an articulating arm mounted to the operating table (not shown). The handle assembly 20 includes first and second arm members 26, 28 hingedly coupled via coupling mechanism shown generally at 30. The second retractor blade 16 is rigidly coupled (generally perpendicularly) to the end of the first arm member 26. The third retractor blade 18 is rigidly coupled (generally perpendicularly) to the end of the second arm member 28. The first retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Through the use of handle extenders 31, 33, the arms 26, 28 may be simultaneously opened such that the second and third retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, and/or an oval cross-section. Optional light emitting devices (not shown) may be coupled to one or more of the retractor blades 12, 16, 18 to direct light down the operative corridor 15.

Figure 16:
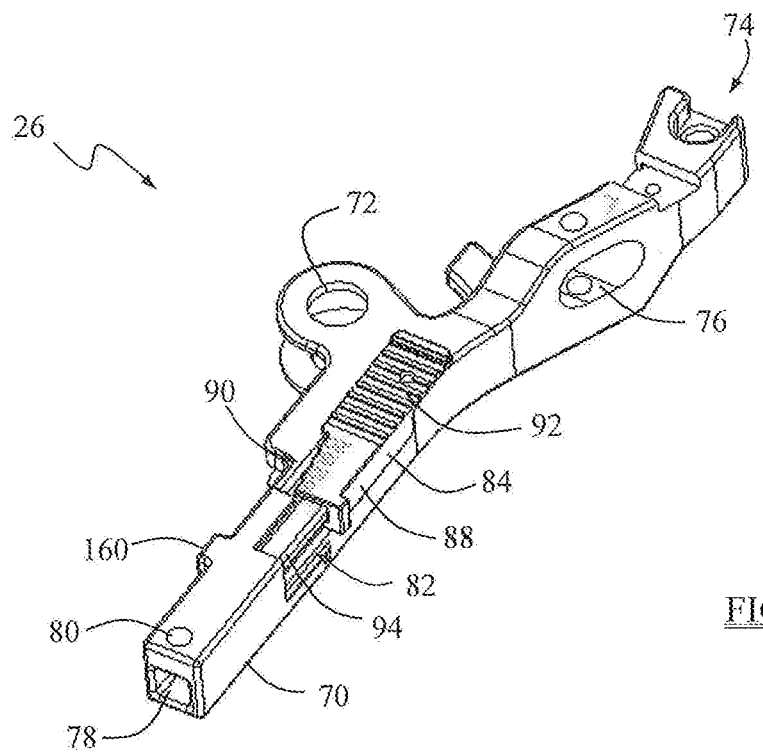
FIGS. 16-17 are perspective views of an arm member comprising part of the tissue retraction assembly of FIG. 1.
Figure 17:
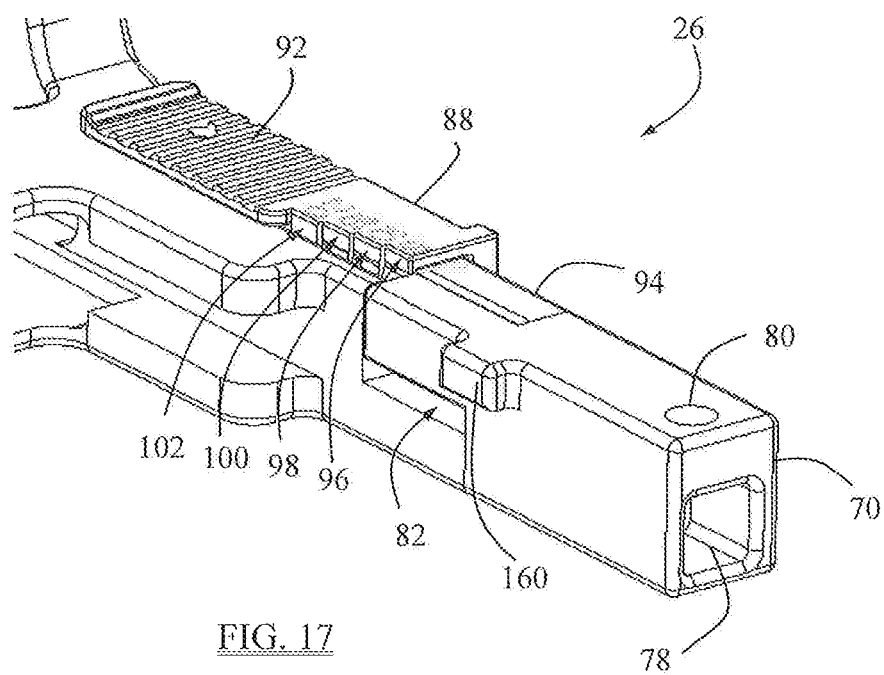
Figure 18:
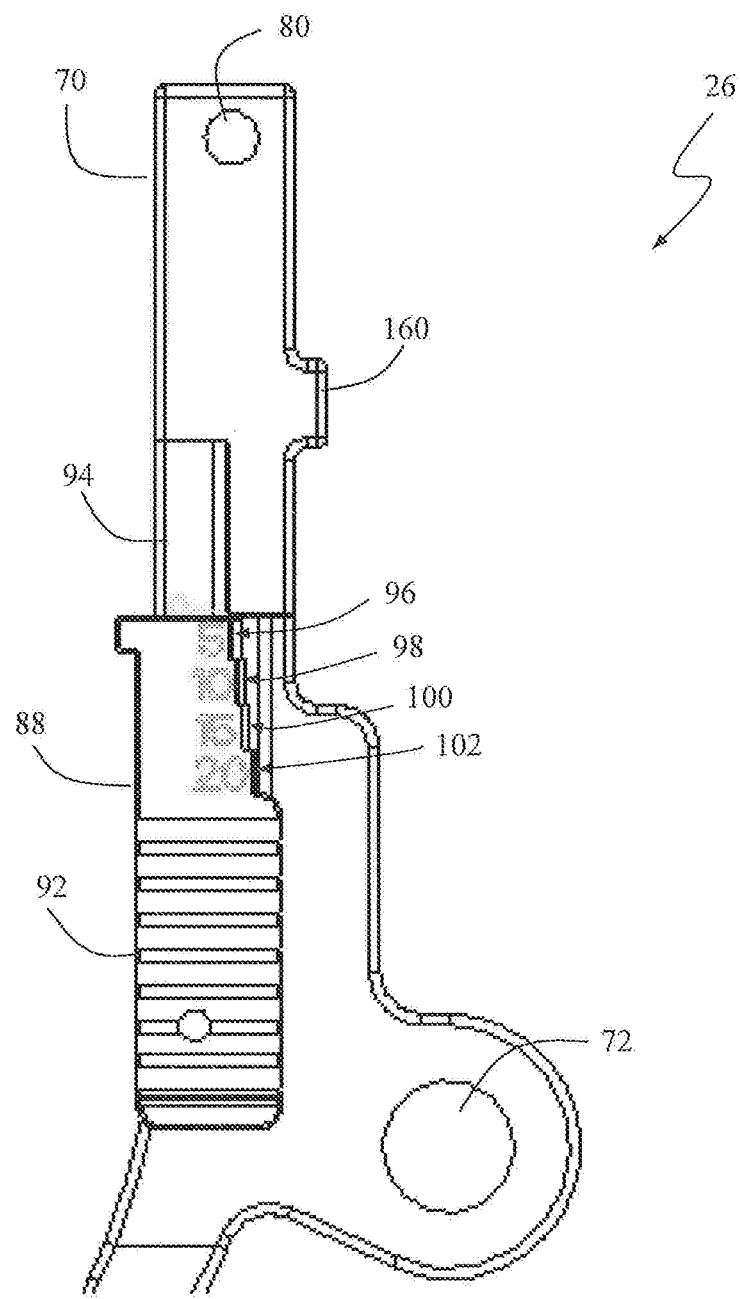
FIG. 18 is a top view of the arm member of FIG. 16.

FIGS. 16-18 illustrate the first arm member 26 in greater detail. First arm member 26 includes a distal pivot member 70, a coupling aperture 72, a proximal region 74 at which handle extender 31 may be attached, an aperture 76 through which knob 36 passes, and a slidable locking mechanism 84 (which may include a single-step lock 86 shown by way of example in FIGS. 14-15 and/or a variable-stop lock 88 as shown in FIGS. 16-18 and described by way of example below). The distal pivot member 70 includes a blade aperture 78, an aperture 80, and a cutout region 82. The blade aperture 78 is dimensioned to interact with the proximal region of the retractor blade 16 in a male-female relationship, such that the male end of blade 16 fits into the female blade aperture 78. To rigidly secure blade 16 to retractor arm 26, a pin or screw (not shown) may be inserted into aperture 80.

The variable-stop lock 88 allows the user to control the degree of expansion of the operative corridor 15. Variable-stop lock 88 includes a variable-stop region 90 and a user engagement region 92, and is dimensioned to slidably engage locking bar 94. The variable-stop region 90 may include any number of sequential step-wise cutout regions corresponding to the angulation desired for the retractor blades 16, 18. By way of example only, the variable-stop locking mechanism includes four sequential step-wise cutout regions 96, 98, 100, 102. Each sequential step-wise cutout region 96, 98, 100, 102 may correspond to a distinct degree of angulation of the retractor blades 16, 18 (relative to the "closed" position shown in FIGS. 2-3). By way of example only, sequential step-wise cutout regions 96, 98, 100, 102 may correspond to 5°, 10°, 15° and 20° of angulation, respectively. Each sequential step-wise cutout region 96, 98, 100, 102 is dimensioned to interact with the distal pivot member 70 once the desired degree of angulation is determined. The user engagement region 92 may include a series of ridges 104 or any other suitable friction-causing element to allow a user to manually operate the variable-stop lock 88 (to adjust and/or lock it).

Figure 19:
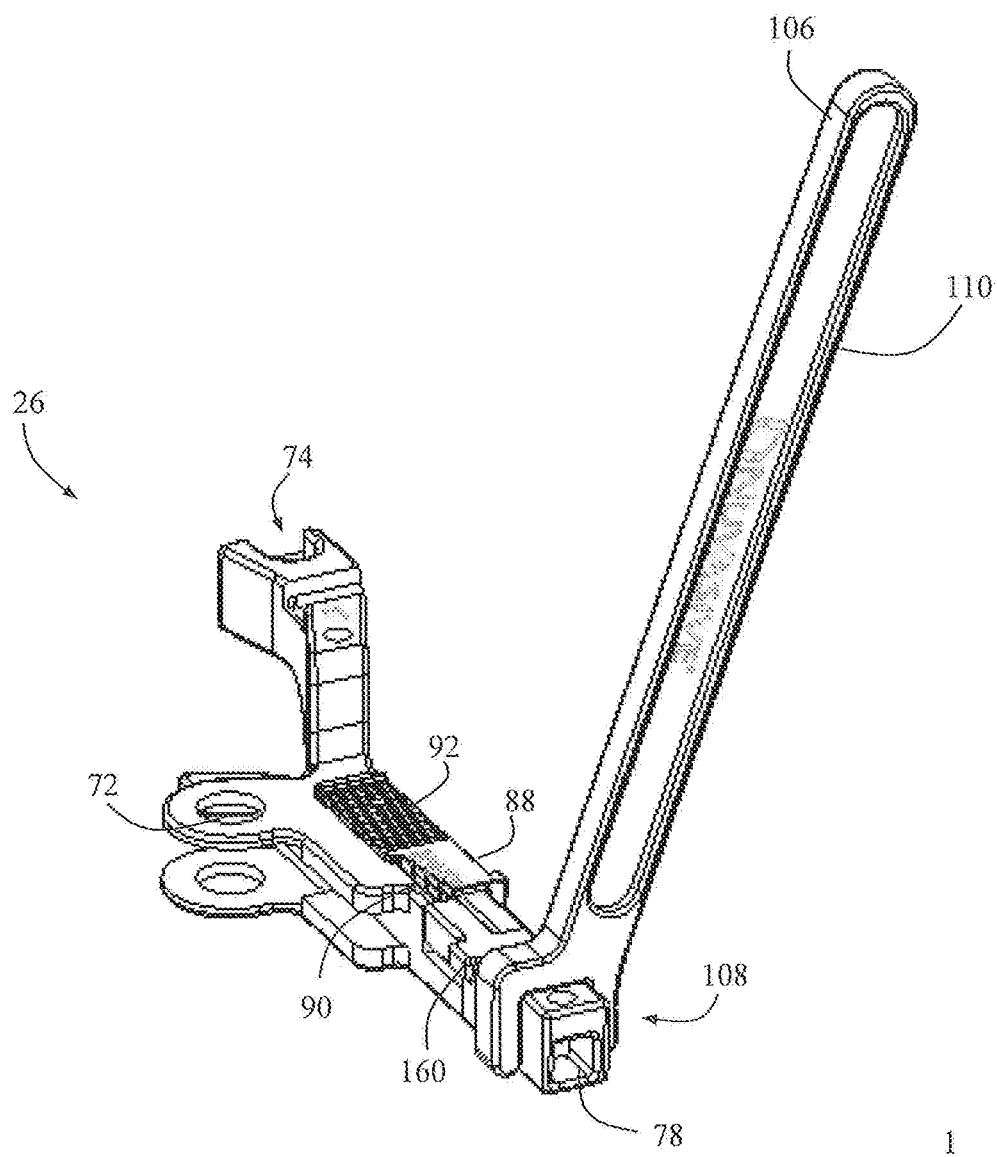
FIGS. 19-20 are perspective and top views, respectively, of the arm member of FIG. 16 in which a pivot wrench is coupled with a distal pivot region of the arm member.
Figure 20:
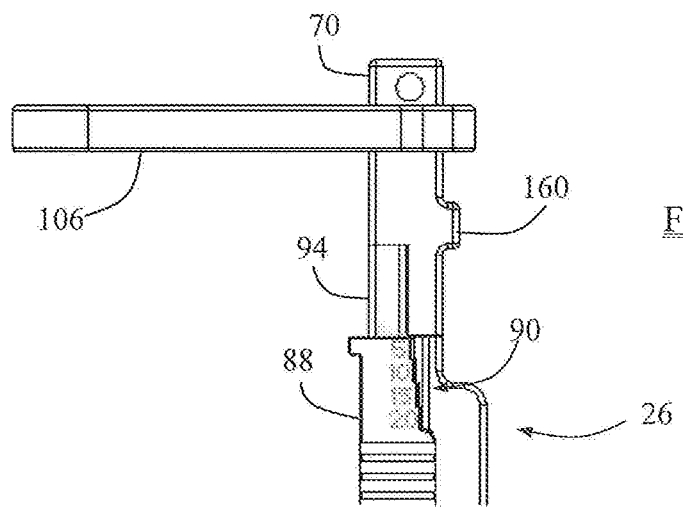
Figure 21:
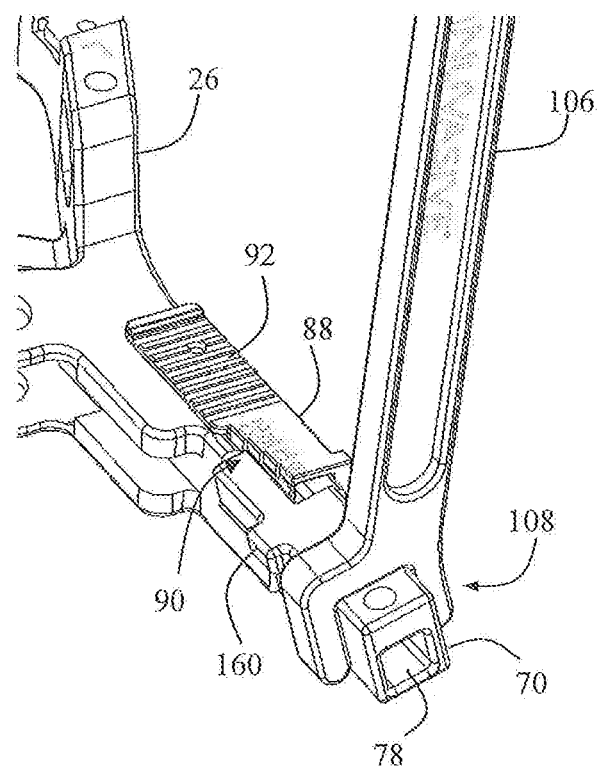
FIG. 21 is a perspective view of the arm member of FIG. 19 after the distal pivot region as been pivoted and the locking mechanism has been engaged.
Figure 22:
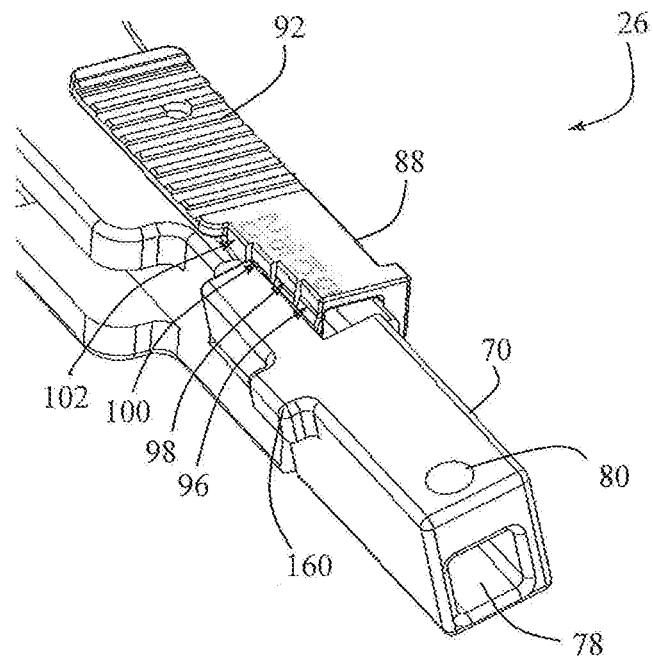
FIGS. 22-23 are perspective and top views, respectively, of the arm member of FIG. 21 in which the pivot wrench has been removed.
Figure 23:
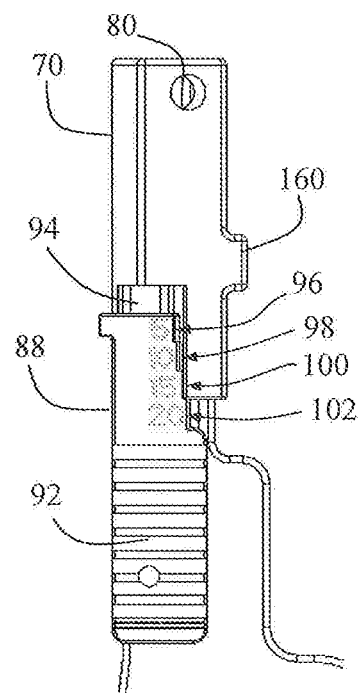
Figure 25:
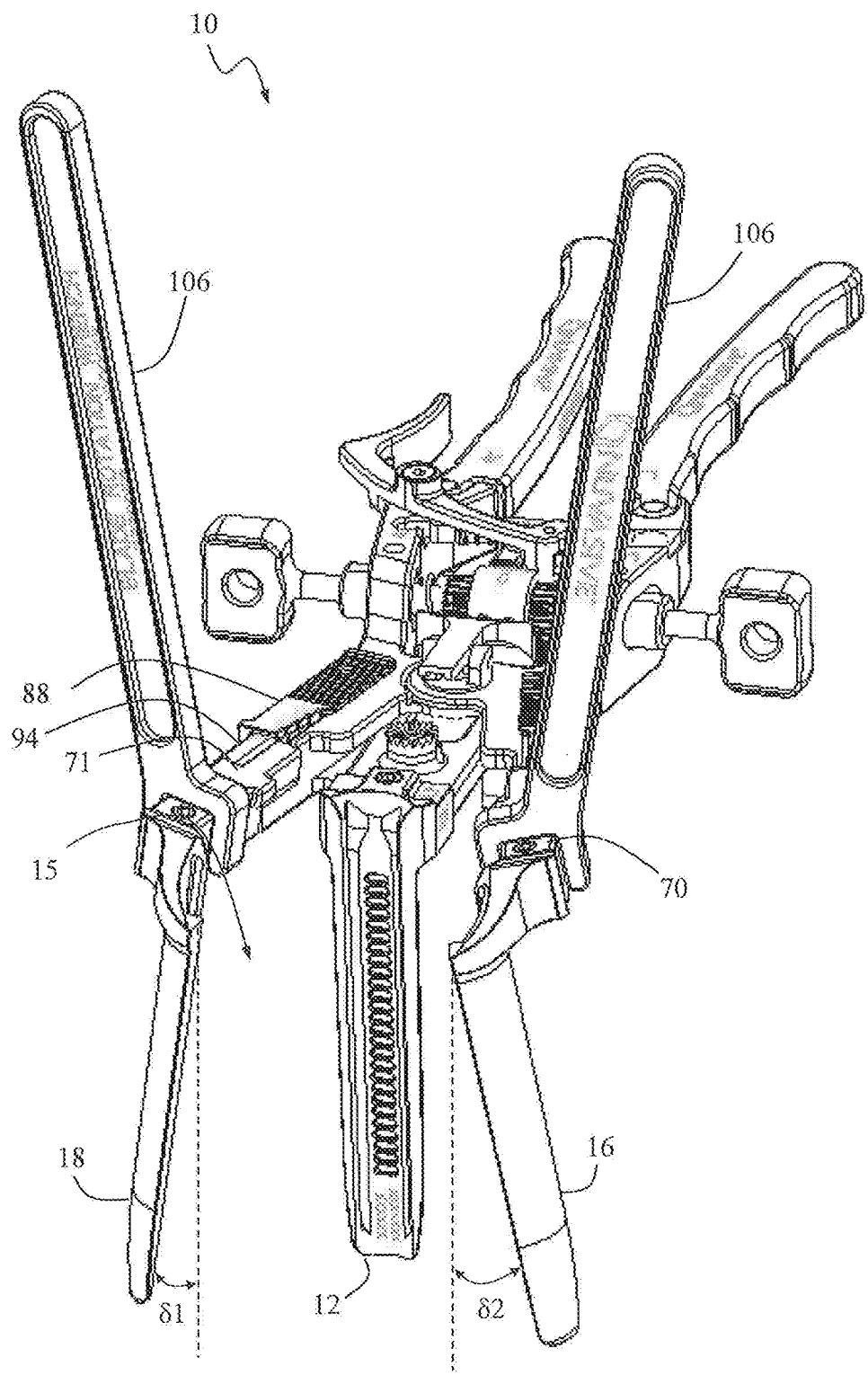
FIG. 25 is a perspective view of the tissue retraction assembly of FIG. 24 after pivoting of the blades.
Figure 26:
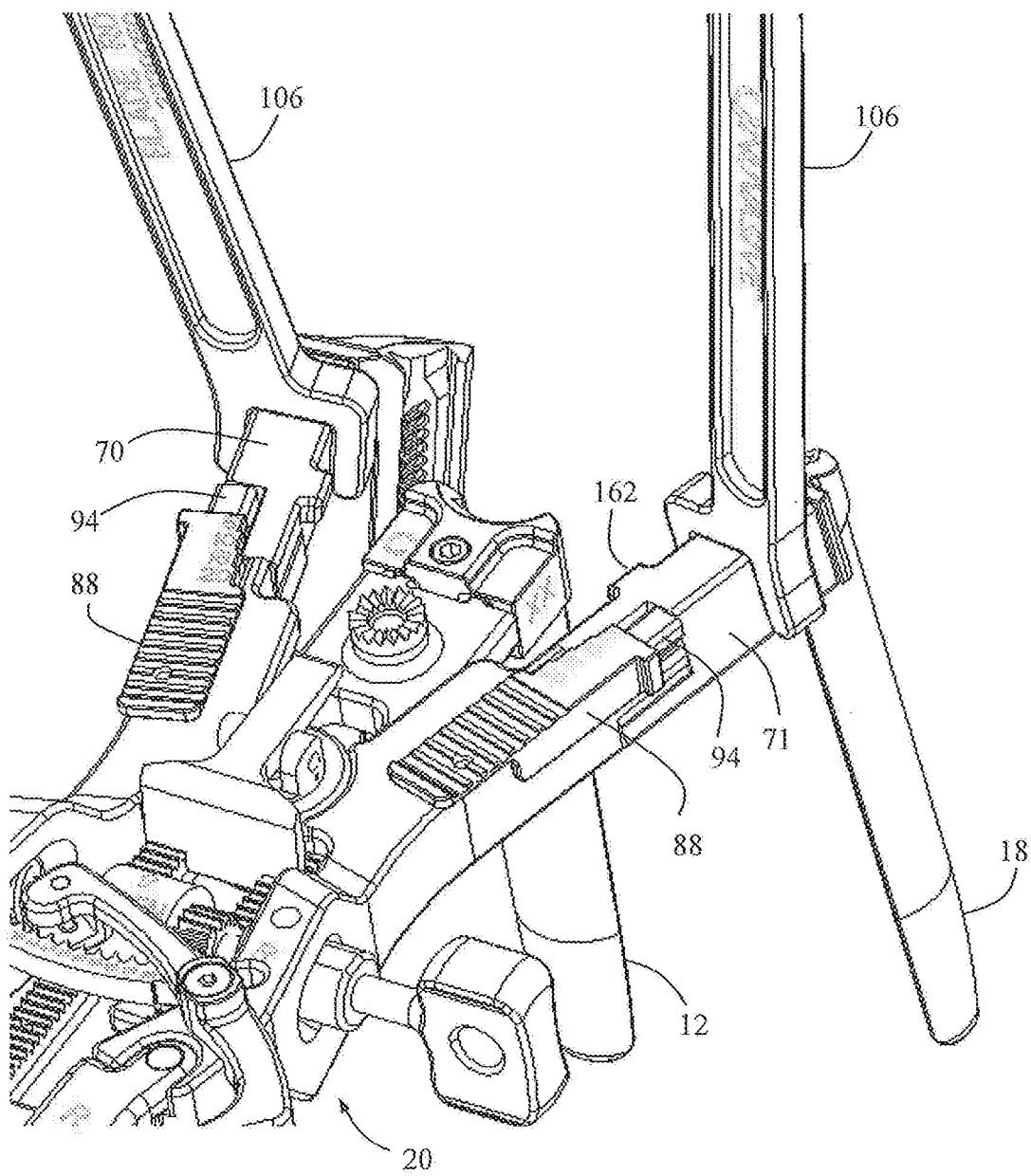
FIG. 26 is a perspective view of the tissue retraction assembly of FIG. 25, in which the locking mechanisms have been activated.
Figure 27:
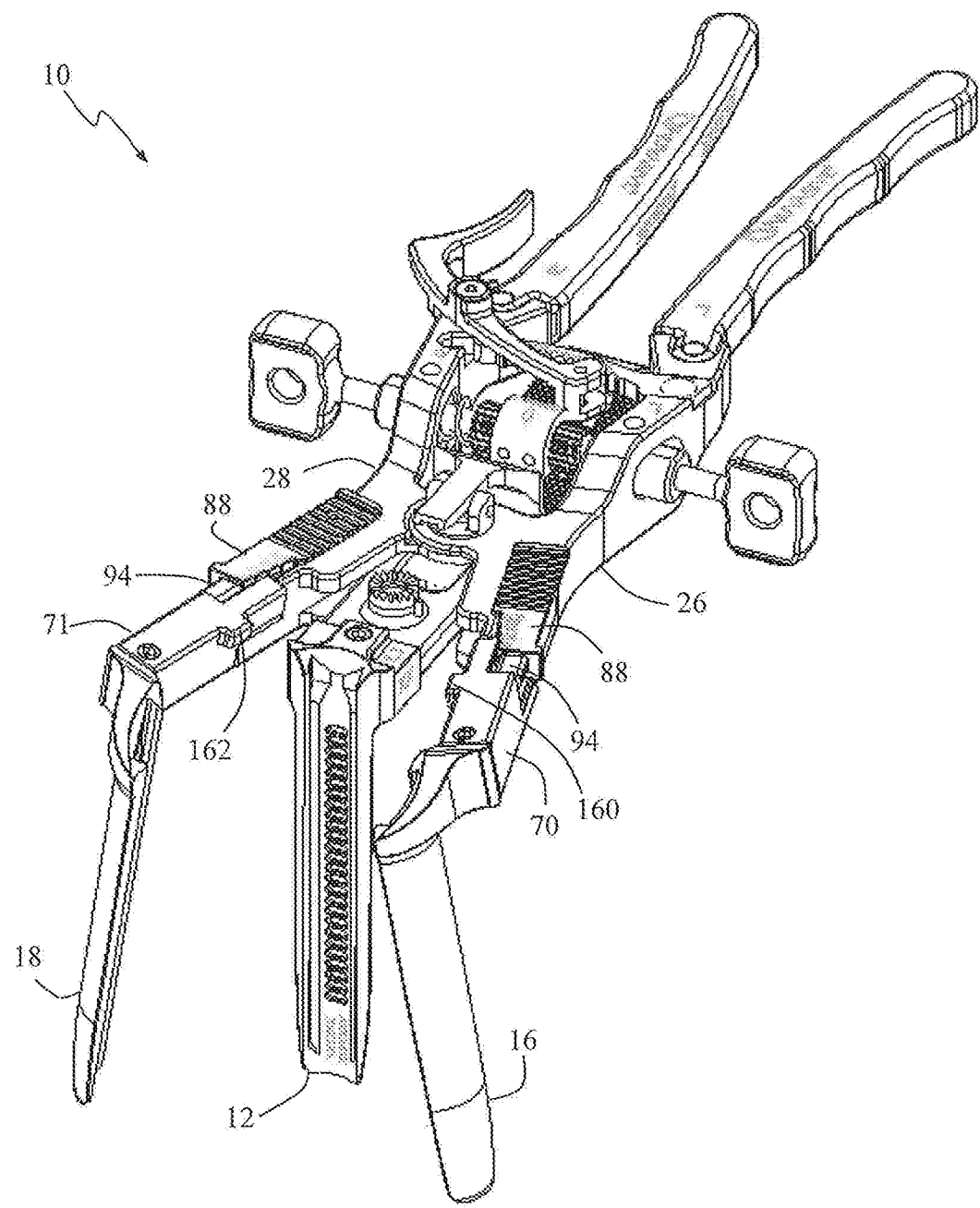
FIGS. 27-28 are perspective and top views, respectively, of the tissue retraction assembly of FIG. 25, in which the cephalad-most and caudal-most blades have been pivoted and the locking mechanisms have been engaged.
Figure 28:
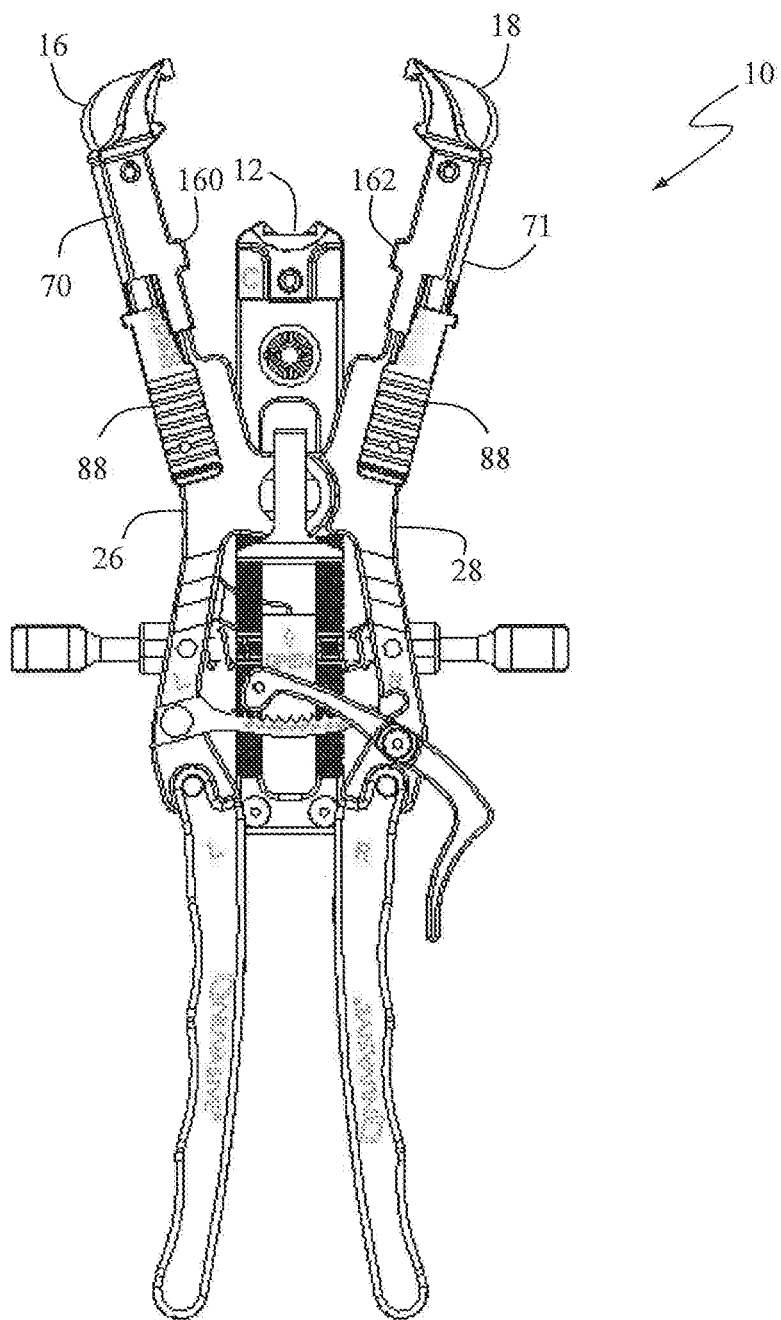
Figure 29:
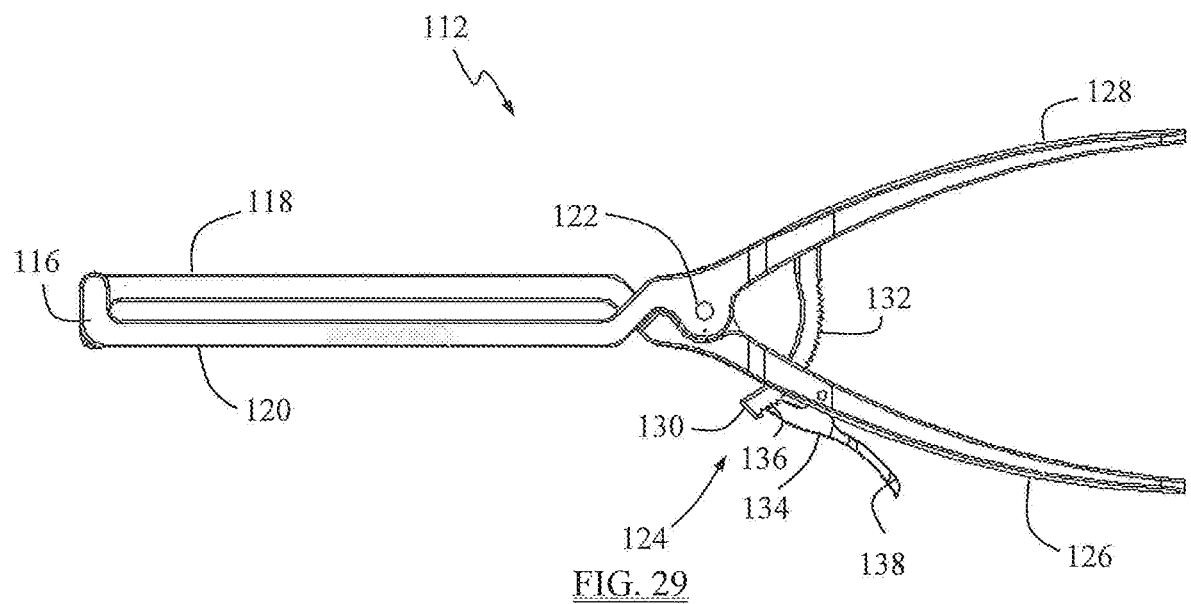
FIGS. 29-30 are side views of a retractor blade expander tool according to one embodiment of the present invention, shown in initial closed and secondary open positions, respectively.
Figure 30:
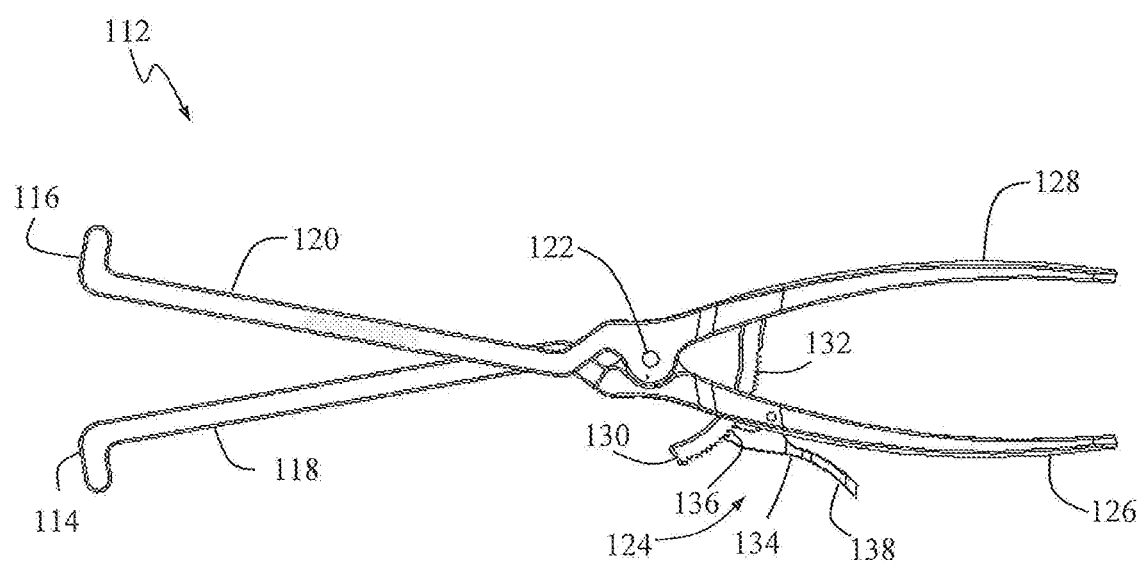

Initially, the retractor assembly 10 of the present invention is introduced to the surgical target site with the retractor blades 12, 16, 18 in a first, closed position (shown generally in FIGS. 2-3). In this configuration, the retractor blades 16, 18 are oriented in a generally perpendicular configuration. In some instances it may be desirable to pivot either the second retractor blade 16 or the third retractor blade 18 (or both) outward in order to increase the volume of the operative corridor 15 (by increasing the distal dimension of the operative corridor). To accomplish this (with respect to blade 16), a pivot wrench 106 is engaged to the distal pivot member 70 of arm 26, as shown in FIGS. 19-21. The pivot wrench 106 includes a gripping portion 108 and a handle 110. The gripping portion 108 is dimensioned to snugly interact with the distal pivot member 70 of arm 26. When the handle 110 is moved in a medial direction (relative to the retractor 10), the blade 16 will pivot in a lateral (outward) direction (FIGS. 21 and 25). Distal pivot member 70 of retractor arm 26 is configured in such a way that it prevents the blade 16 from pivoting in a medial direction. In this manner, the blade 16 may be pivoted to a desired angulation (any angle between 0 and 45 degrees from center, denoted by δ1 & δ2 in FIG. 25). While maintaining this desired angulation, the user may engage the user engagement region 92 and exert a force to slide the variable-stop lock 88 in a distal direction along locking bar 94 (FIGS. 22 and 26) until the sequential step-wise cutout region 96, 98, 100, 102 corresponding to the particular angulation engages the distal pivot member 70 of the first arm member 26. By way of example only, if a 5° angulation is desired, cutout region 96 will interact with the distal pivot member 70, preventing further pivoting of the retractor blade 16. On the other hand, if a 15° angulation is desired, the variable-stop lock 88 should be moved along locking bar 94 until cutout region 100 interacts with the distal pivot member 70 (shown by way of example in FIGS. 22-23). After engaging the variable-stop lock 88, the pivot wrench 106 may be removed because the retractor blades 16, 18 are locked into a desired degree of angulation (FIGS. 27-28).

Although described with reference to first arm member 26, it will be appreciated that the detailed features and operation of the present invention as embodied within first arm member 26 are generally applicable (though in a mirror-image orientation) to the second arm member 28. Furthermore, the blade 18 may be pivoted independently of blade 16 such that different angles for each blade 16, 18 are achieved. Thus, it may be desirable to use blades of differing lengths and still maintain a symmetrical operating corridor wherein the distal ends of blades 16, 18 are oriented along the same general plane. Before removing the tissue retraction system 10 from the operative corridor, the variable-stop lock 88 should be disengaged by sliding it in a proximal direction along locking bar 94, allowing retractor blades 16, 18 to return to an initial alignment to facilitate removal.

As an alternative to the pivot wrench 106, a blade expander 112, such as shown by way of example only in FIGS. 29-33, may be provided to facilitate the manual pivoting of the retractor blades 16, 18. The blade expander 112 may include first and second blade engagement members 114, 116 located on first and second elongated extenders 118, 120, respectively, a pivot joint 122, a locking element 124 and pair of handle extensions 126, 128. By way of example only, the locking element 124 may include a generally curved member 130 including a series of engagement features 132 located along one edge. By way of example only, the engagement features 132 may consist of a series of "teeth" having a generally triangular cross-section. The locking element 124 may further include a release member 134 including a series of engagement features 136 that interact with engagement features 132 to effectively lock the blade expander 112 in a second variable configuration. The release member 134 further includes a manual depressor 138 that, when depressed, causes engagement features 136 to disengage from engagement features 132, allowing blade expander 112 to return from a second configuration to a first configuration.

Figure 31:
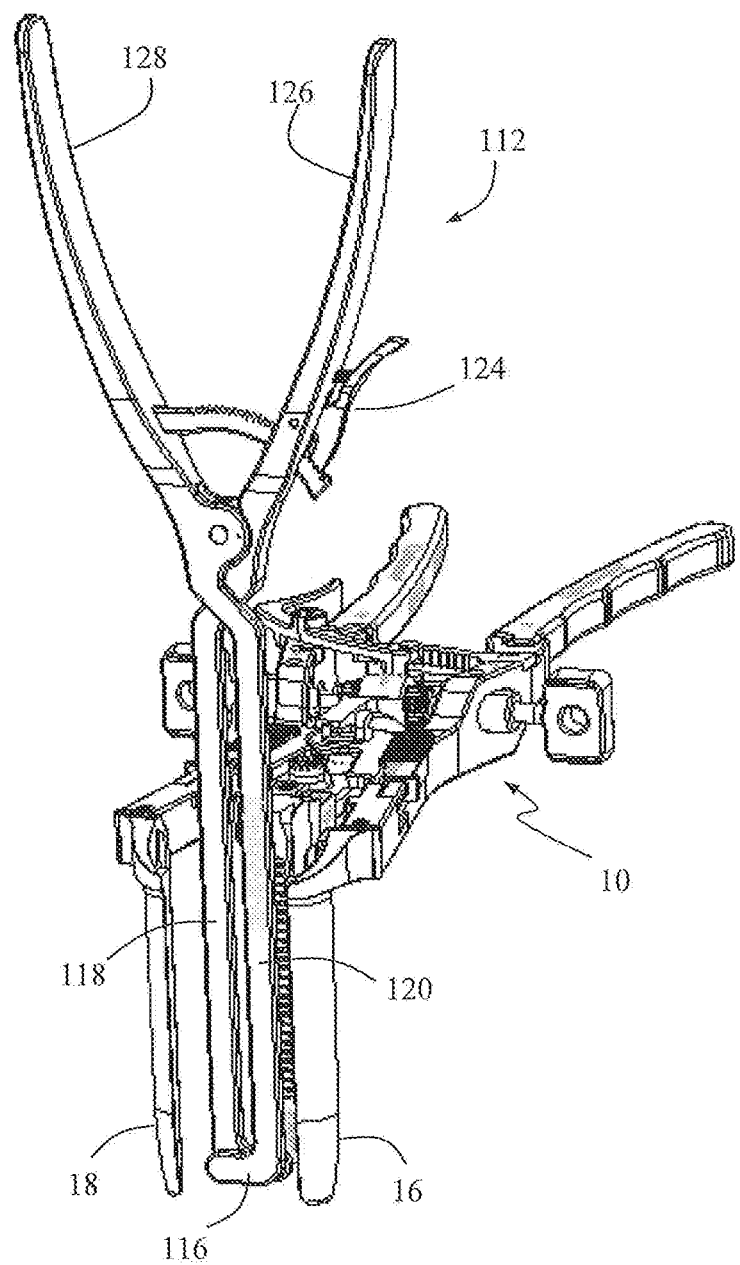
FIG. 31 is a perspective view of a retractor blade expander tool of FIG. 29 inserted into an operative corridor formed by the tissue retraction assembly of FIG. 1 with the blades in a retracted position.
Figure 32:
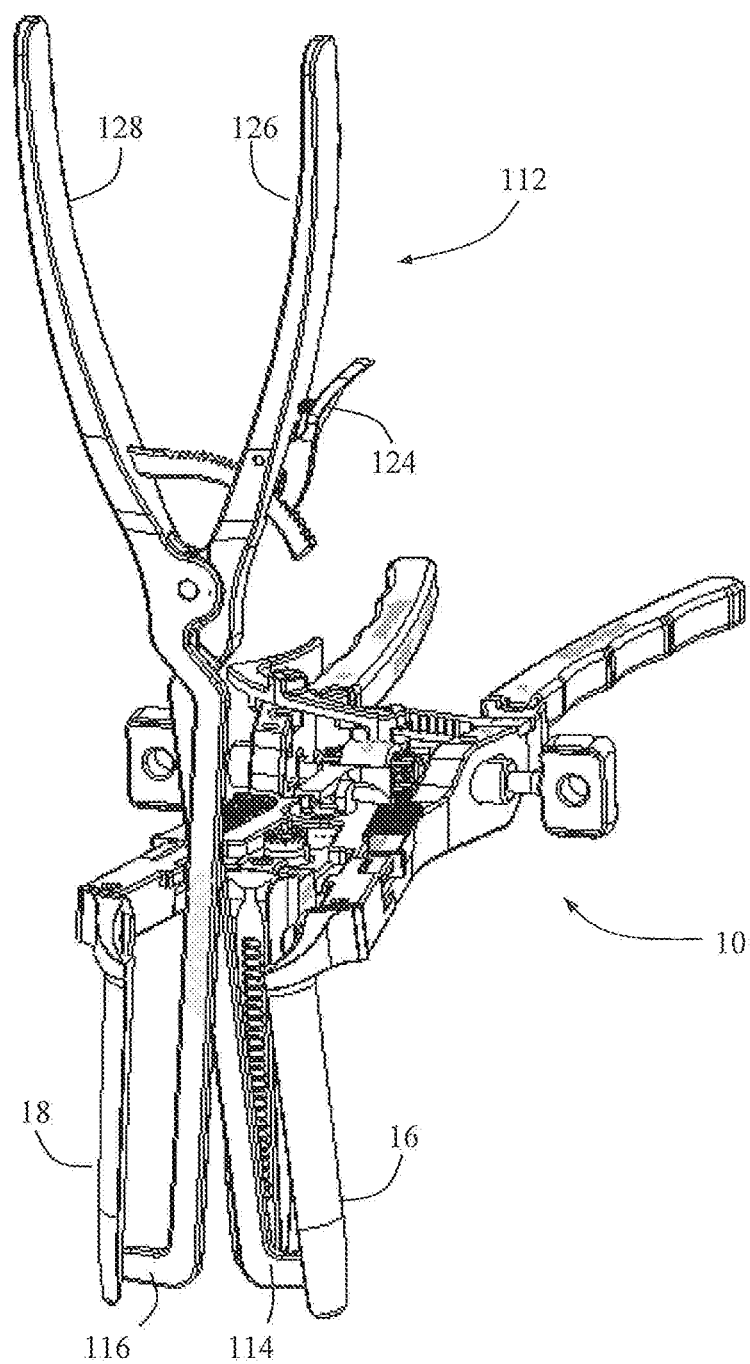
FIGS. 32-33 are perspective views of the retractor blade expander tool of FIG. 31 in an open/position causing the cephalad-most and caudal-most retractor blades of the tissue retraction assembly of FIG. 31 to pivot in an outward direction.
Figure 33:
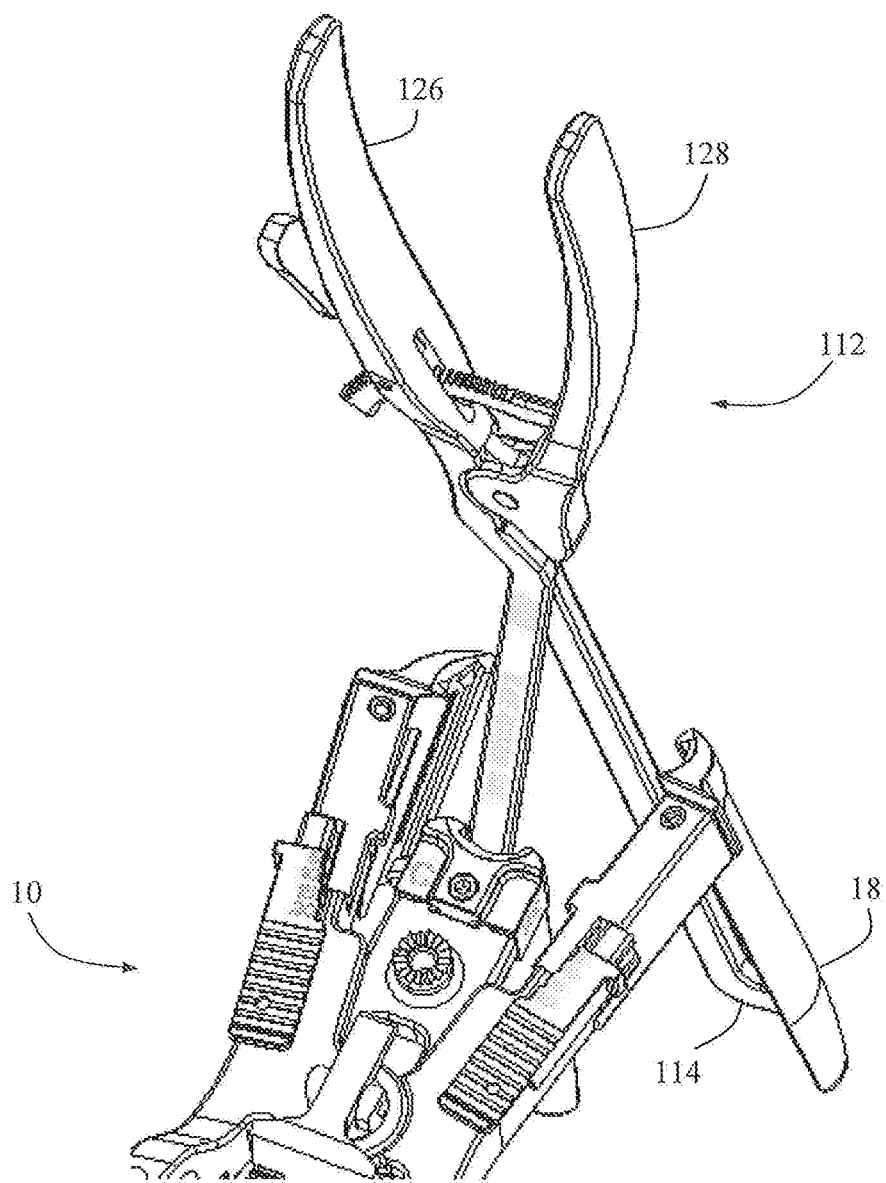
Figure 34:
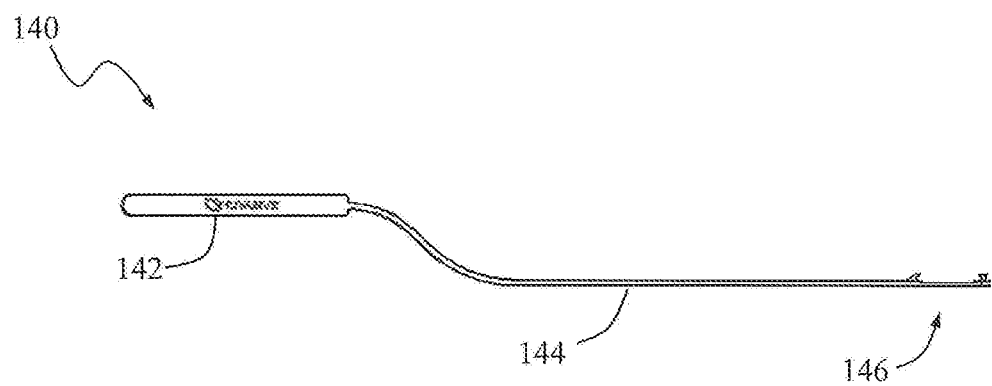
FIGS. 34-35 are side and perspective views, respectively, of a shim inserter according to a preferred embodiment of the present invention.
Figure 35:
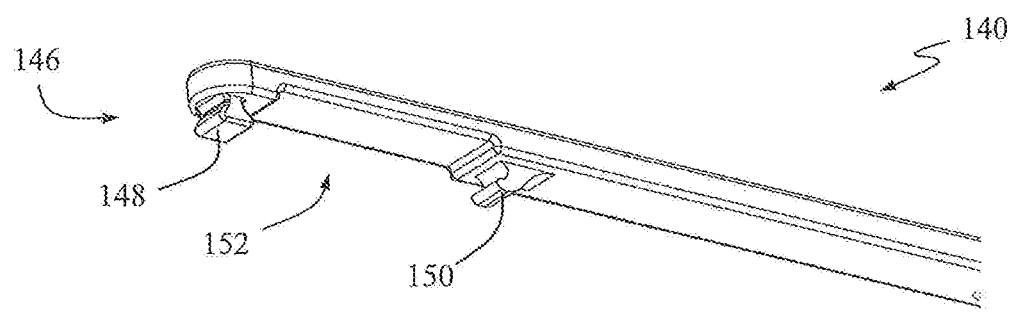

With the retractor blades 16, 18 in an initial alignment (i.e. generally perpendicular to the handle 20) and the first and second arm members 26, 28 in an "open" position, the blade expander 112 may be inserted into the operative corridor in a first "closed" position, as shown by way of example in FIG. 31. The blade engagement members 114, 116 may be positioned to interact with the retractor blades 16, 18, respectively. The user may then operate the blade expander 112 by squeezing handle extensions 126, 128, thereby causing first and second elongated extenders 118, 120 to spread apart into a second "open" position shown generally in FIG. 30. Blade engagement members 114, 116 are thus forced against the retractor blades 16, 18, causing distal pivot members 70, 71 to pivot in an outward direction (shown by way of example in FIGS. 32-33). Once the desired degree of angulation (secondary alignment) of the retractor blades 16, 18 is achieved, the user should cease squeezing the handle extensions 126, 128. Due to the interaction between engagement features 132, 136 of the locking element 124, the blade expander 112 is effectively locked in this second position. When desired, the blade expander 112 may be returned to a first closed position by engaging manual depressor 138 on release member 134, allowing blade expander 112 to be removed from the operative corridor 15.

Figure 36:
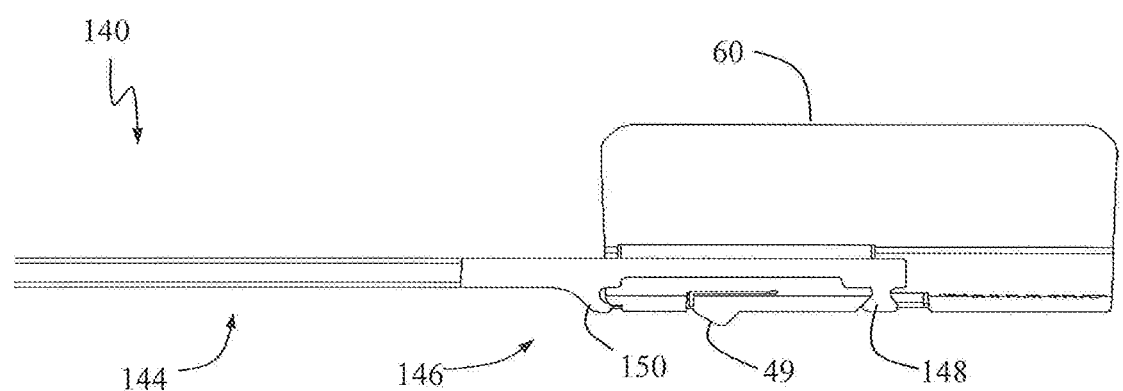
FIGS. 36-37 are side and perspective views, respectively, the shim inserter of FIG. 34 coupled to a shim.
Figure 37:
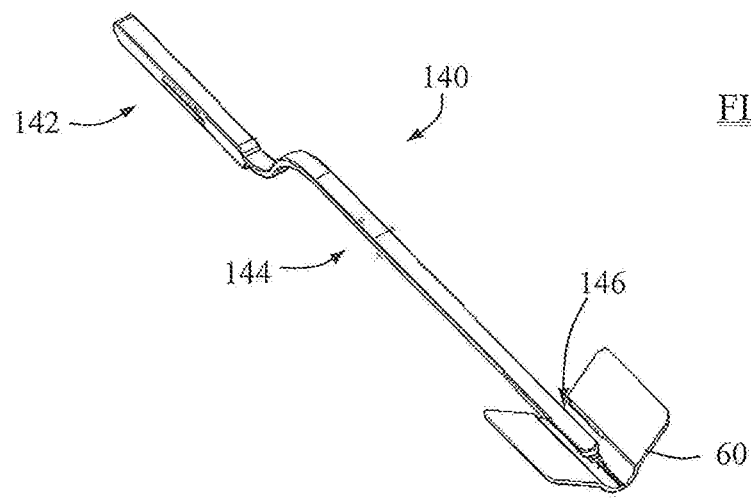

FIGS. 34-38 illustrate an inserter 140 for inserting retractor extenders 22, 24, 60 and/or shim element 25 according to a preferred embodiment of the present invention. By way of example only, inserter 140 is shown and described herein in conjunction with retractor extender 60, although it is to be readily appreciated that the inserter 140 may be employed in a similar manner with retractor extenders 22, 24 and shim element 25 according to the present invention. Inserter 140 includes a handle 142, and elongated region 144, and a distal end 146. The handle 142 may be any configuration suitable to allow purchase with the human hand, including but not limited to a grip (composed of any suitable material including but not limited to rubber, plastic, or metal) or a T-handle. The elongated region 144 may be straight or included any number of curved regions, and may be of any length necessary to mate the retractor extender 60 with the retractor blade 16/18. The distal end 146 may include a distal stub 148, a grip protrusion 150, and a recessed region 152. The distal stub 148 is configured to interact with elongated slot 43 of retractor extender 60 such that the retractor extender 60 is rigid relative to the inserter 140. Grip protrusion 150 is dimensioned to engage snugly over the edge of retractor extender 60 such that the retractor extender 60 is locked into place on the inserter 140 (FIG. 36).

Figure 38:
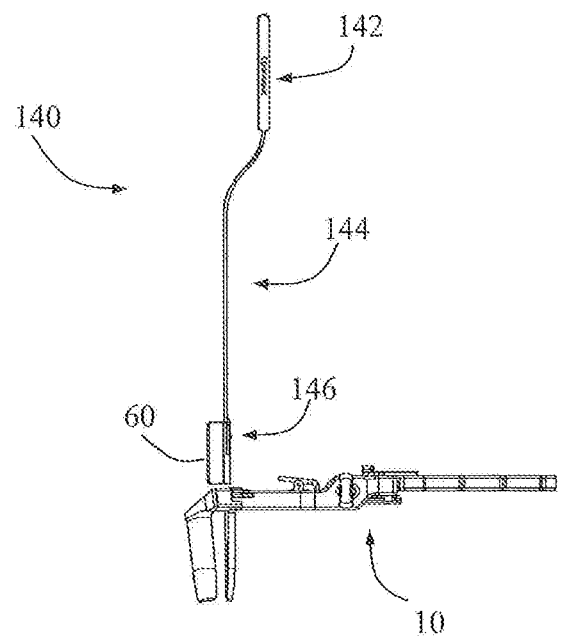
FIGS. 38-39 are side and top views, respectively, of the shim inserter of FIG. 36 prior to insertion of the shim.
Figure 39:
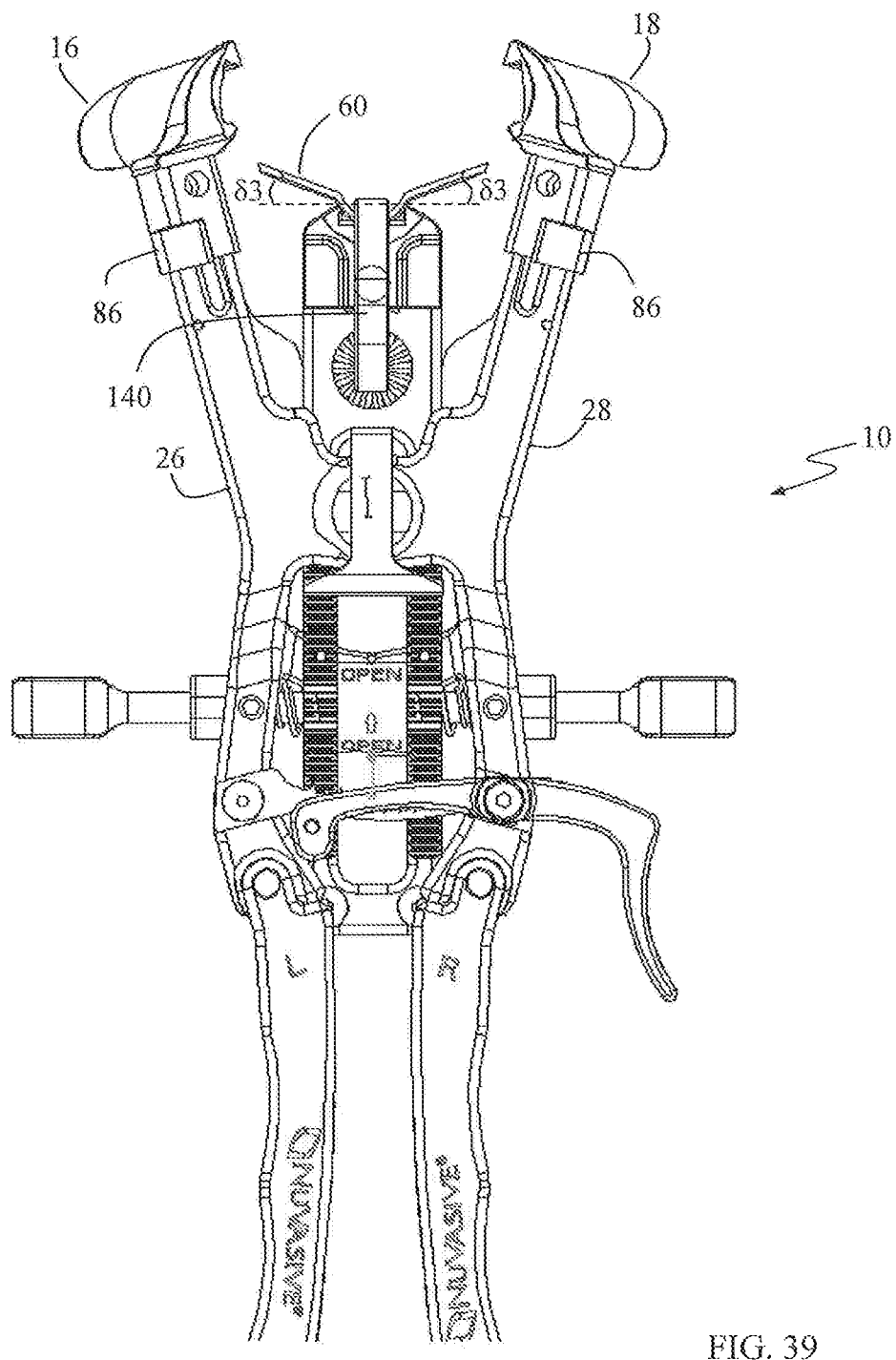
Figure 40:
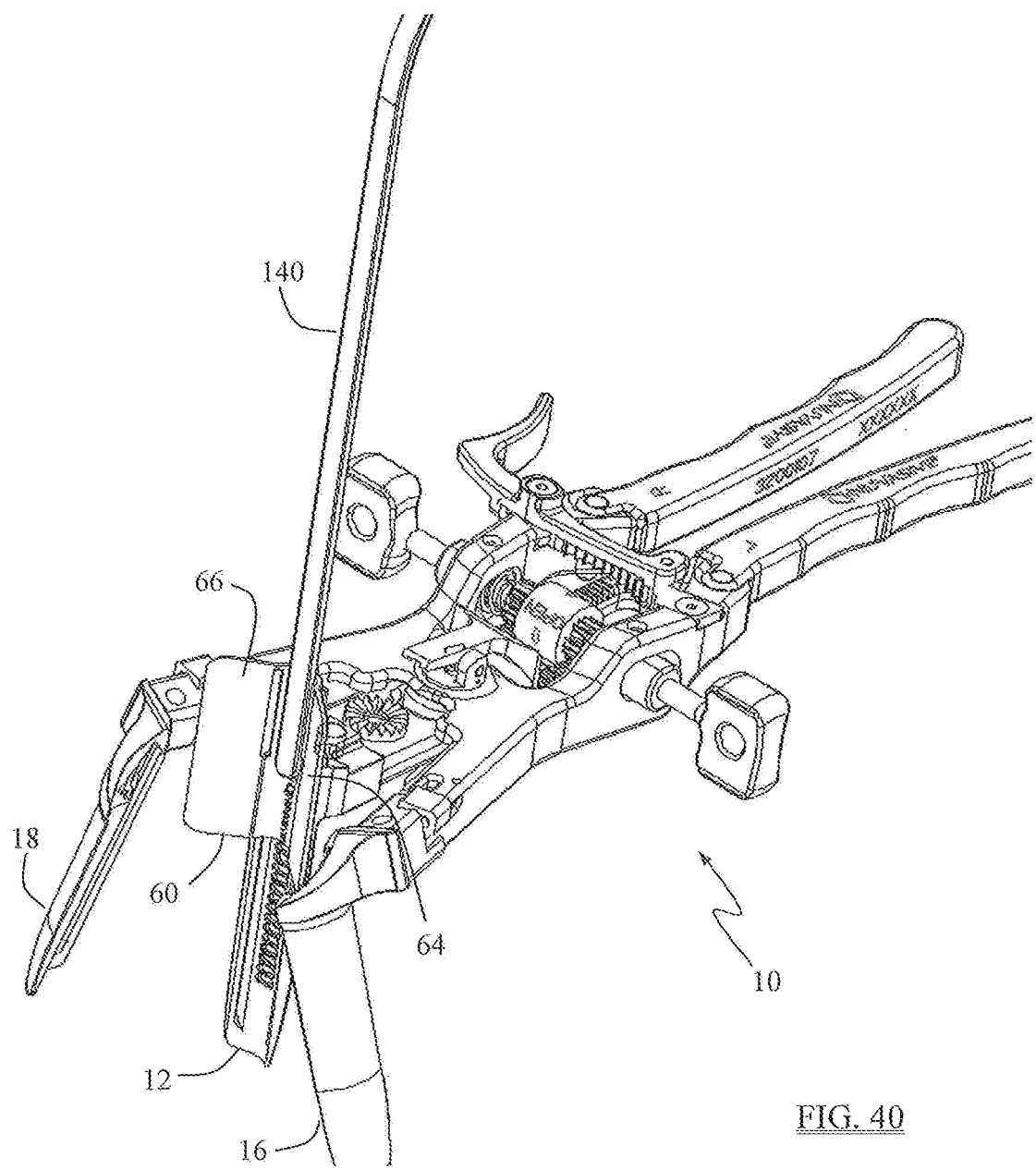
FIGS. 40-41 are perspective and top views, respectively, of a shim inserter according to the present invention coupled to a shim in the initial phase of insertion, where the shim is entering the operative corridor at the skin level.
Figure 41:
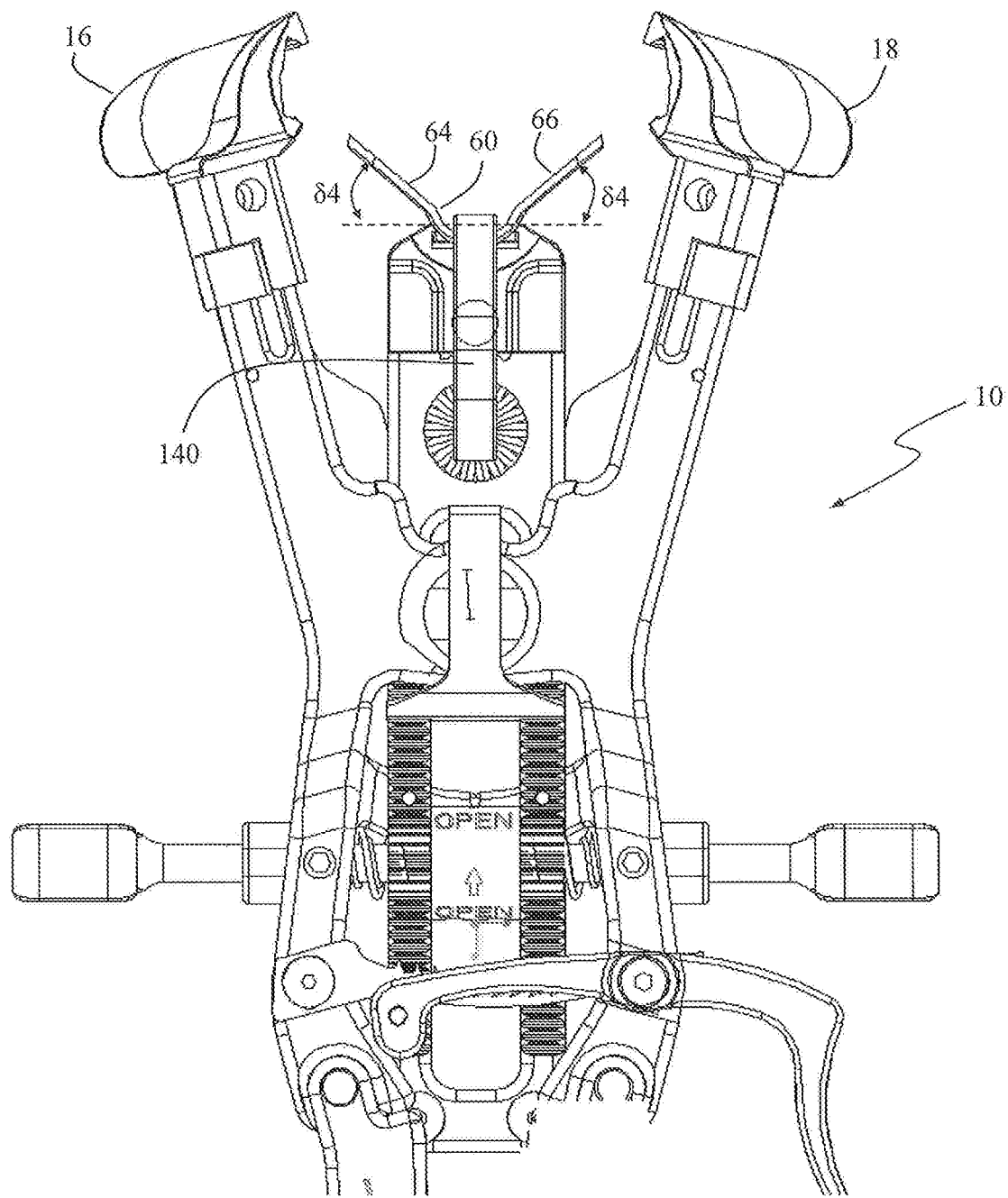
Figure 42:
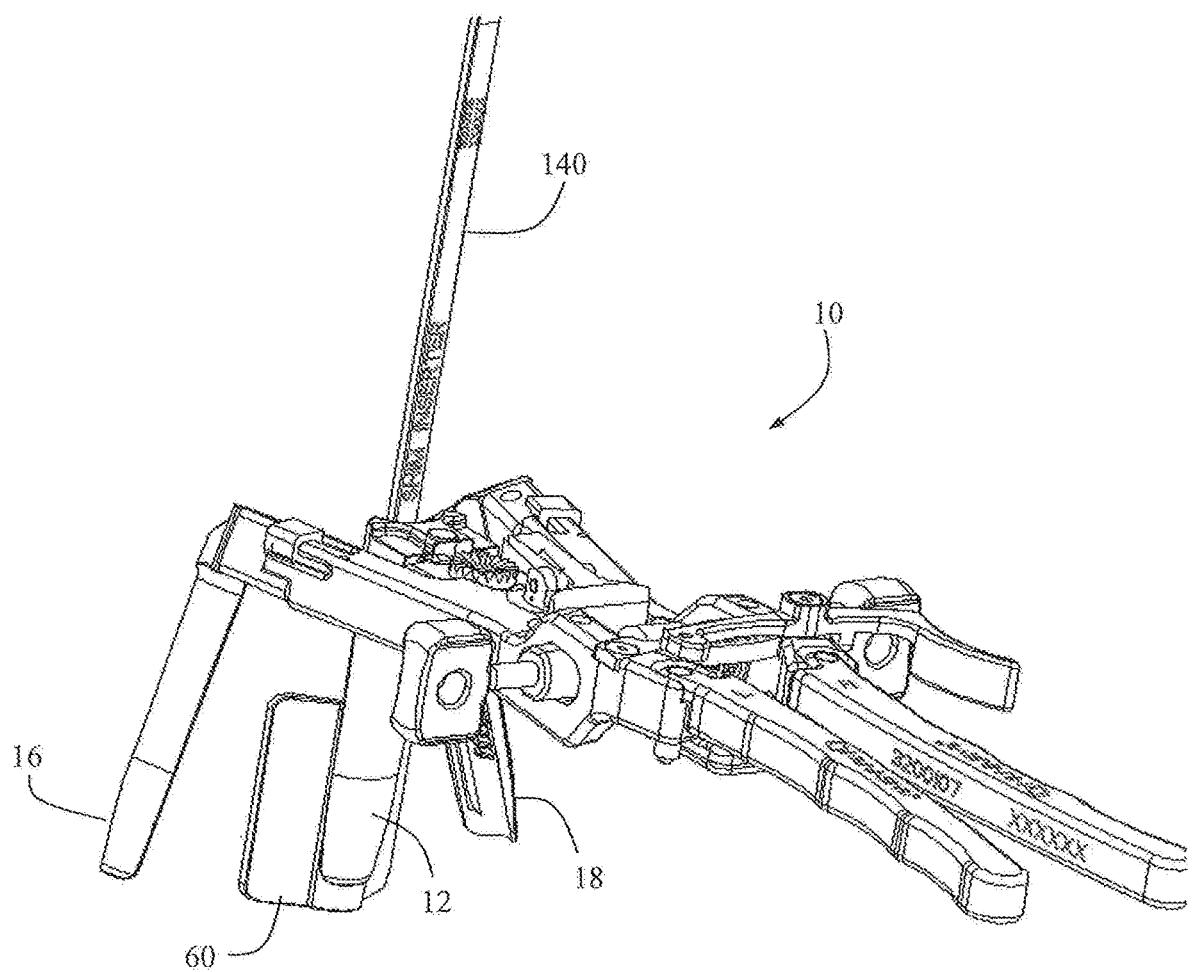
FIGS. 42-43 are perspective and top views, respectively, of the shim inserter & shim of FIG. 52, where the shim has been inserted beyond the skin level and fully into the operative corridor.
Figure 43:
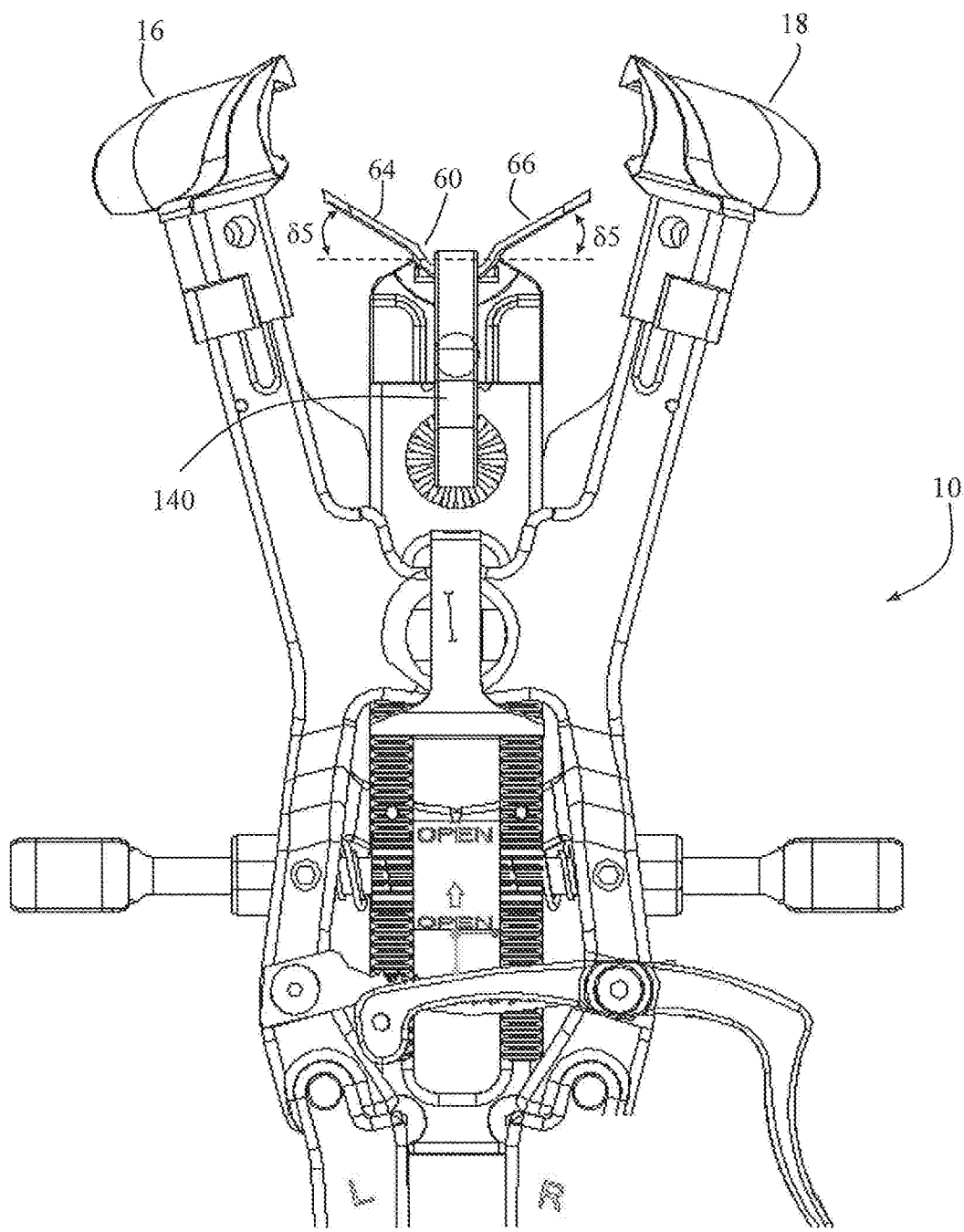
Figure 44:
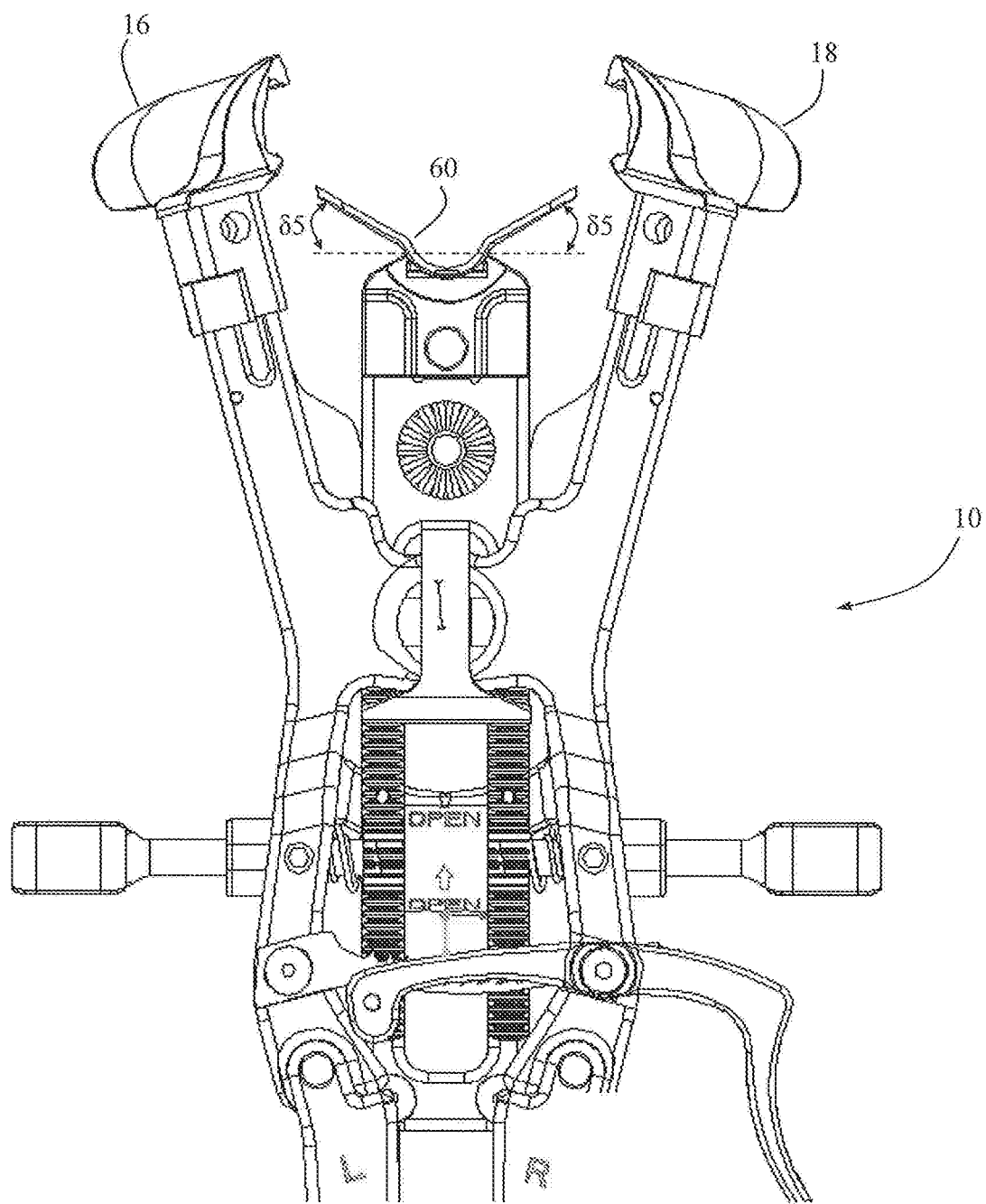
FIGS. 44-45 are top and perspective views, respectively, of a fully inserted shim, wherein the shim inserter has been removed.
Figure 45:
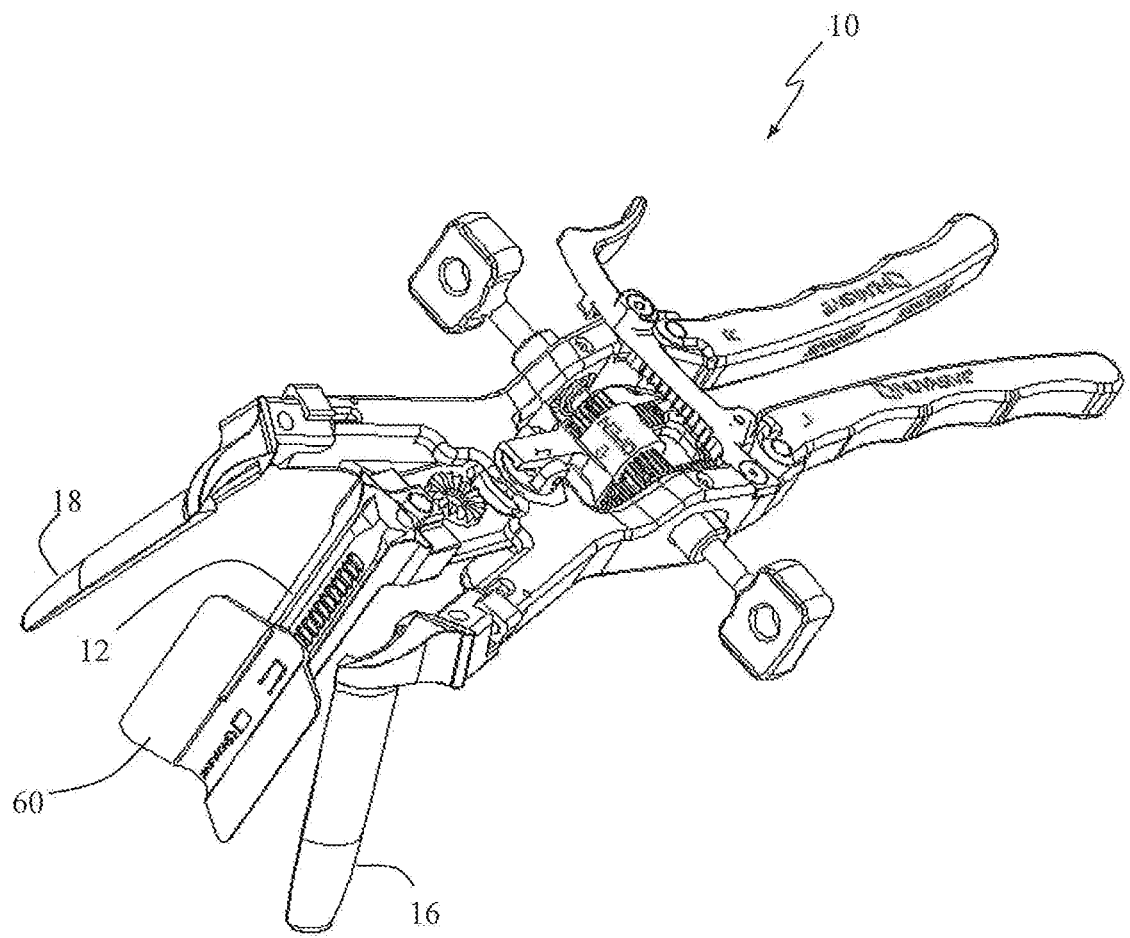

In use, once the retractor extender 60 is attached to the inserter 140 (FIG. 37), the retractor extender 60/inserter 140 combination is positioned over the desired retractor blade (shown as the posterior blade 12 in FIG. 38). As the retractor extender 60 is inserted through the operative opening at the level of the skin (FIGS. 40-41), the retractor extender 60 may compress together such that the panels 64, 66 are oriented at a greater angle (denoted by 54 in FIG. 41) than at default position (denoted by 53 in FIG. 39). As the retractor extender 60 is inserted beyond the level of the skin and into the operative corridor 15 (FIGS. 42-43), the panels 64, 66 may expand to a lesser angle (denoted by 85 in FIG. 43), which may or may not be the same angle as in default position. Once the retractor extender 60 has been inserted onto the retractor blade 12, the inserter 140 may be removed (FIGS. 44-45).

Figure 46:
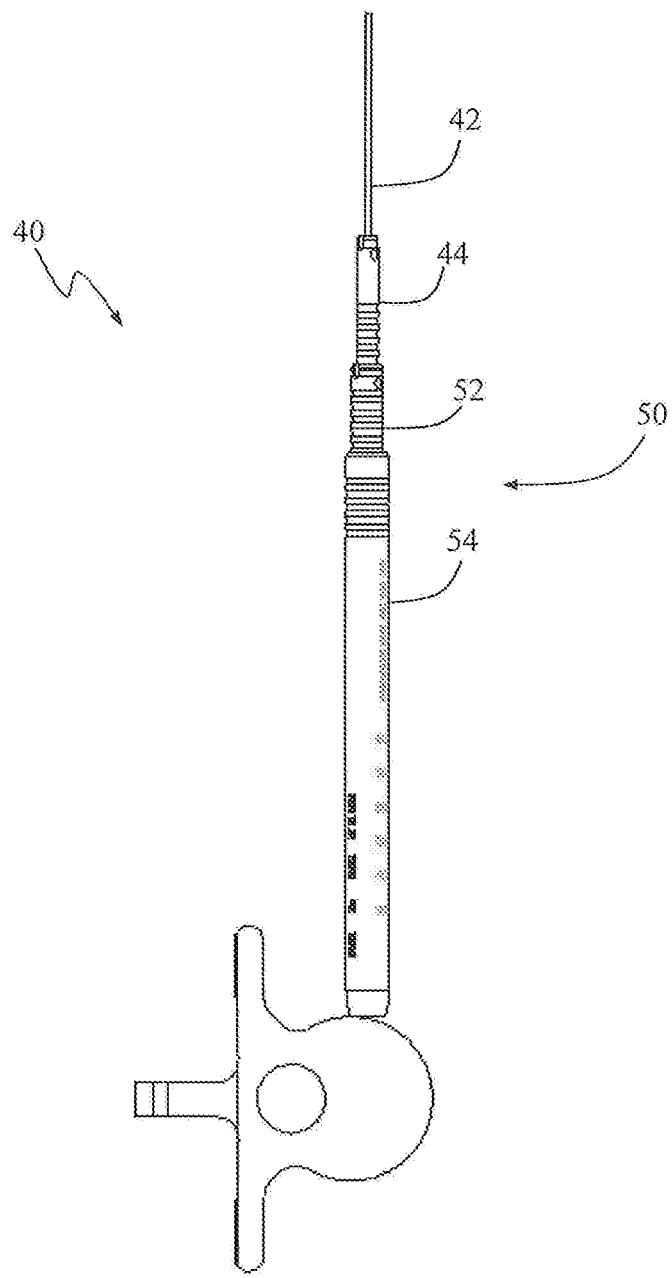
FIG. 46 is a side view illustrating the use of a tissue distraction assembly (comprising a plurality of dilating cannulae over a K-wire) to distract tissue between the skin of the patient and the surgical target site according to the present invention.

FIG. 46 illustrates a tissue distraction assembly 40 forming part of the surgical access system according to the present invention. The tissue distraction assembly 40 includes a K-wire 42, an initial dilating cannula 44, and a sequential dilation system 50. In use, the K-wire 42 is disposed within the initial dilating cannula 44 and the assembly is advanced through the tissue towards the surgical target site (e.g. annulus). Again, this is preferably accomplished while employing the nerve detection and/or direction features described above. After the initial dilating assembly is advanced such that the distal end of the initial dilator 44 is positioned within the disc space, the sequential dilation system 50 consisting of one or more supplemental dilators 52, 54 may be employed for the purpose of further dilating the tissue down to the surgical target site. Once again, each component of the sequential dilation system 50 (namely, the K-wire 42 and the supplemental dilators 52, 54) may be, according to the present invention, provided with one or more electrodes (preferably at their distal regions) equipped for use with a nerve surveillance system, such as, by way of example, the type shown and described in the NeuroVision PCT Applications.

Figure 47:
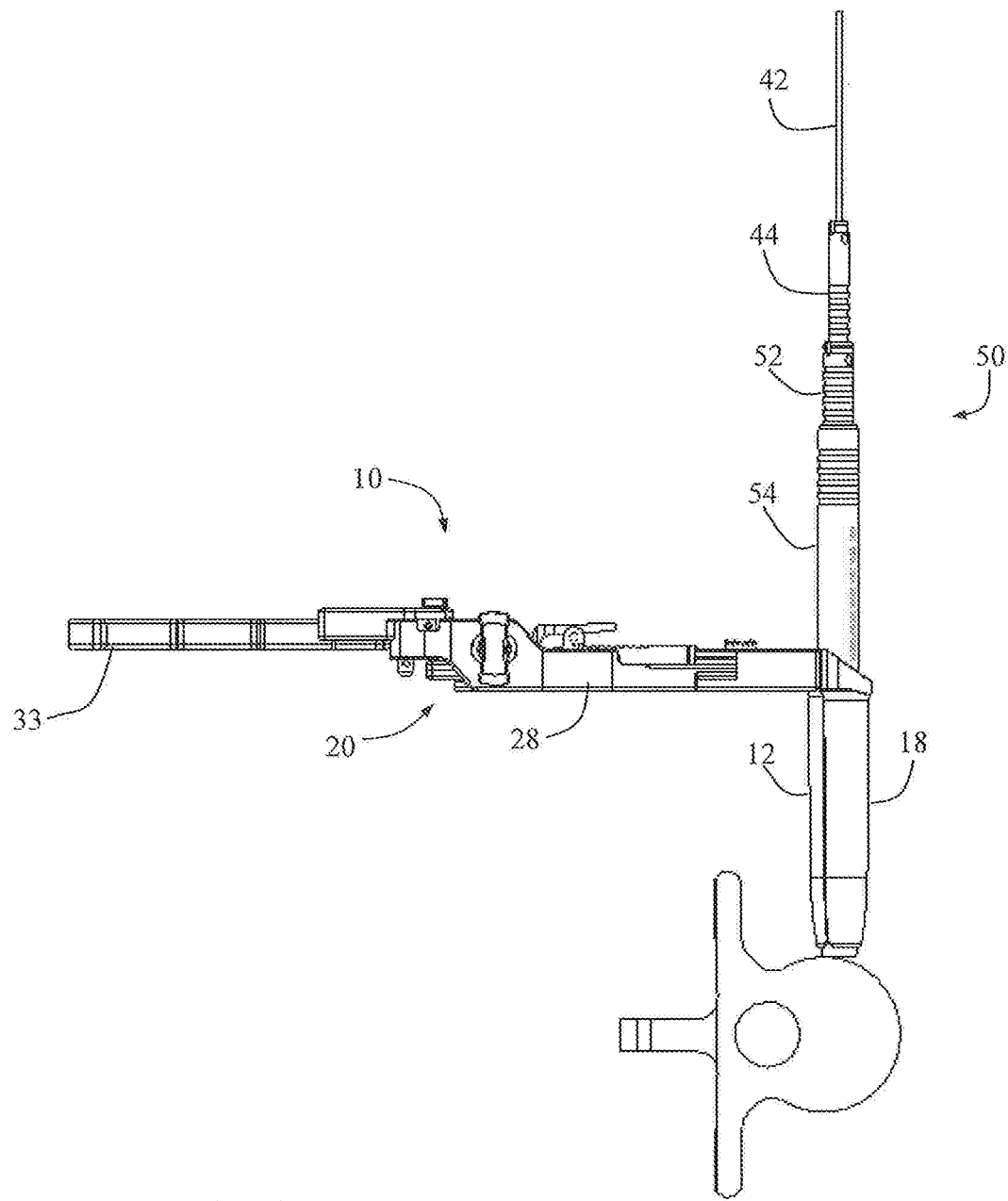
FIG. 47 is a side view of a retractor assembly according to the present invention, comprising a handle assembly having three (3) retractor blades extending there from (posterior, cephalad-most, and caudal-most), shown in a first, closed position and disposed over the tissue distraction assembly of FIG. 46.
Figure 48:
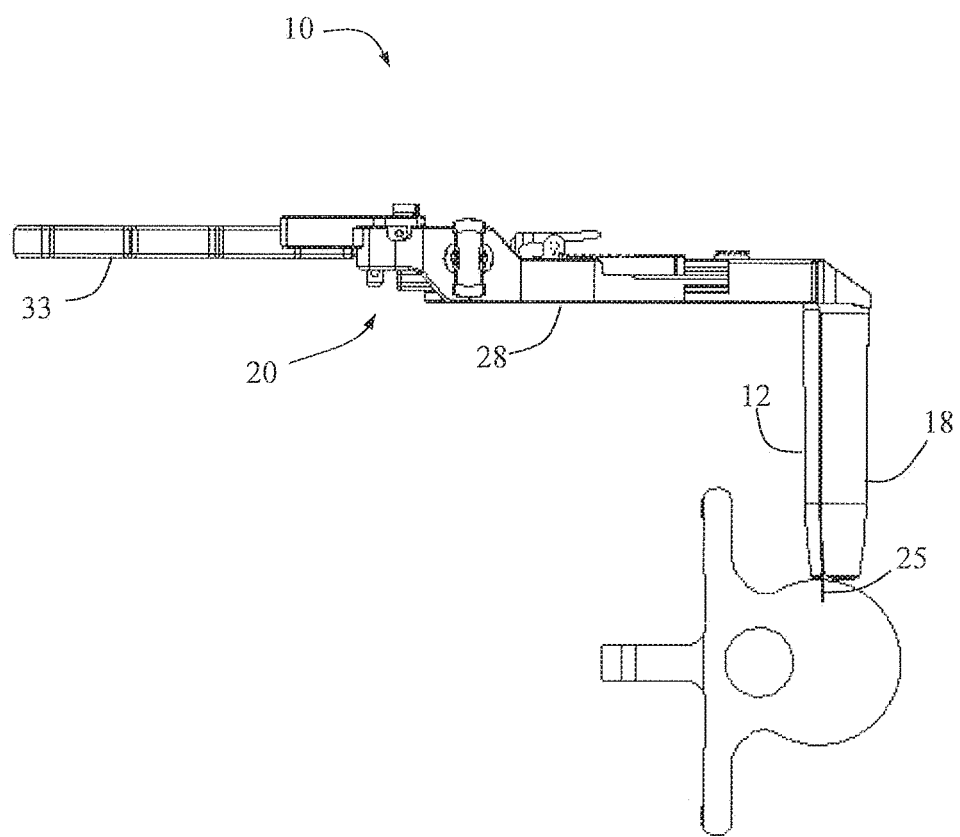
FIG. 48 is a side view of a retractor assembly according to the present invention, comprising a handle assembly having three (3) retractor blades extending there from (posterior, cephalad-most, and caudal-most) with the tissue distraction assembly of FIG. 46 removed and shim element introduced.
Figure 49:
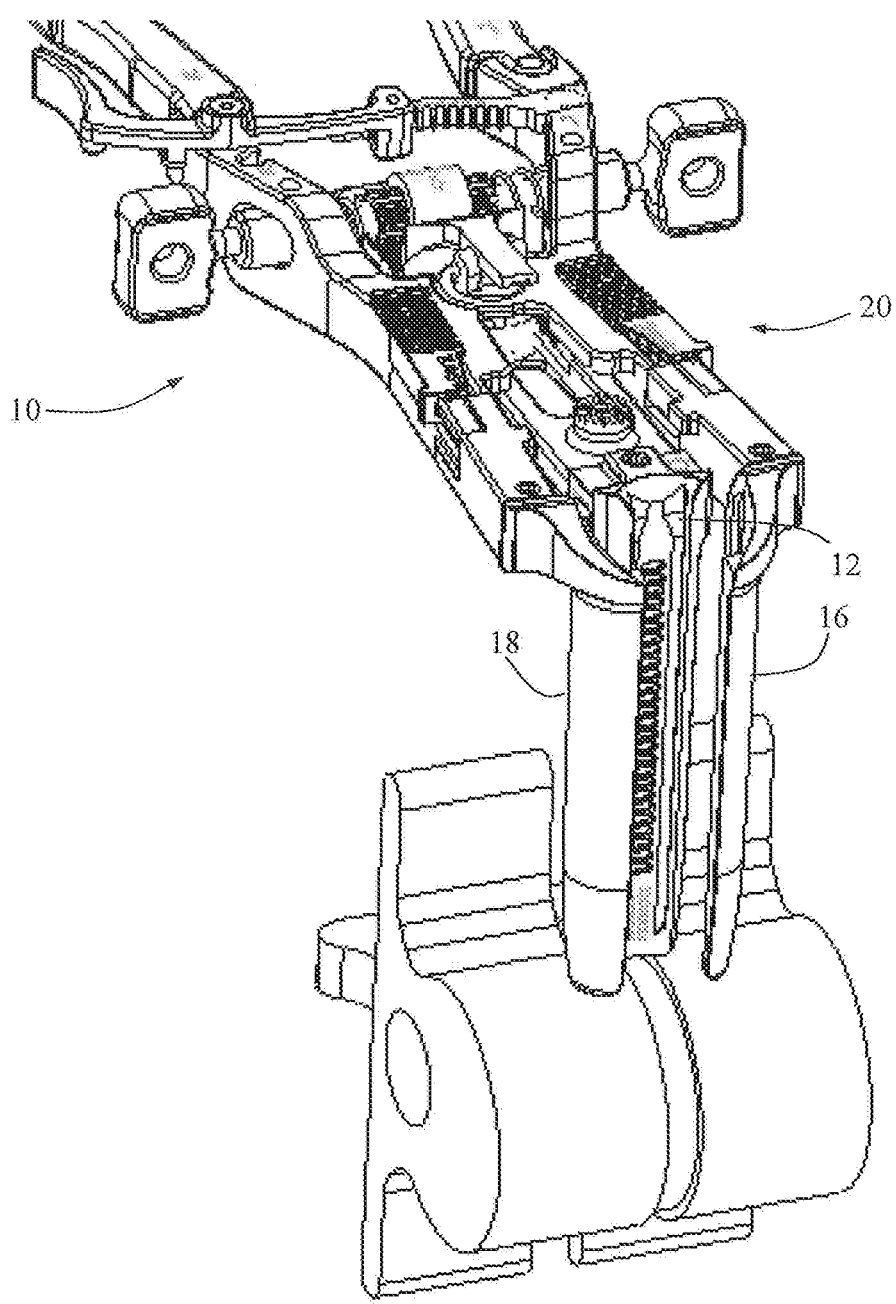
FIG. 49-50 are perspective and top views, respectively, of the retractor assembly in a second, opened (i.e. retracted) position to thereby create an operative corridor to a surgical target site according to the present invention.
Figure 50:
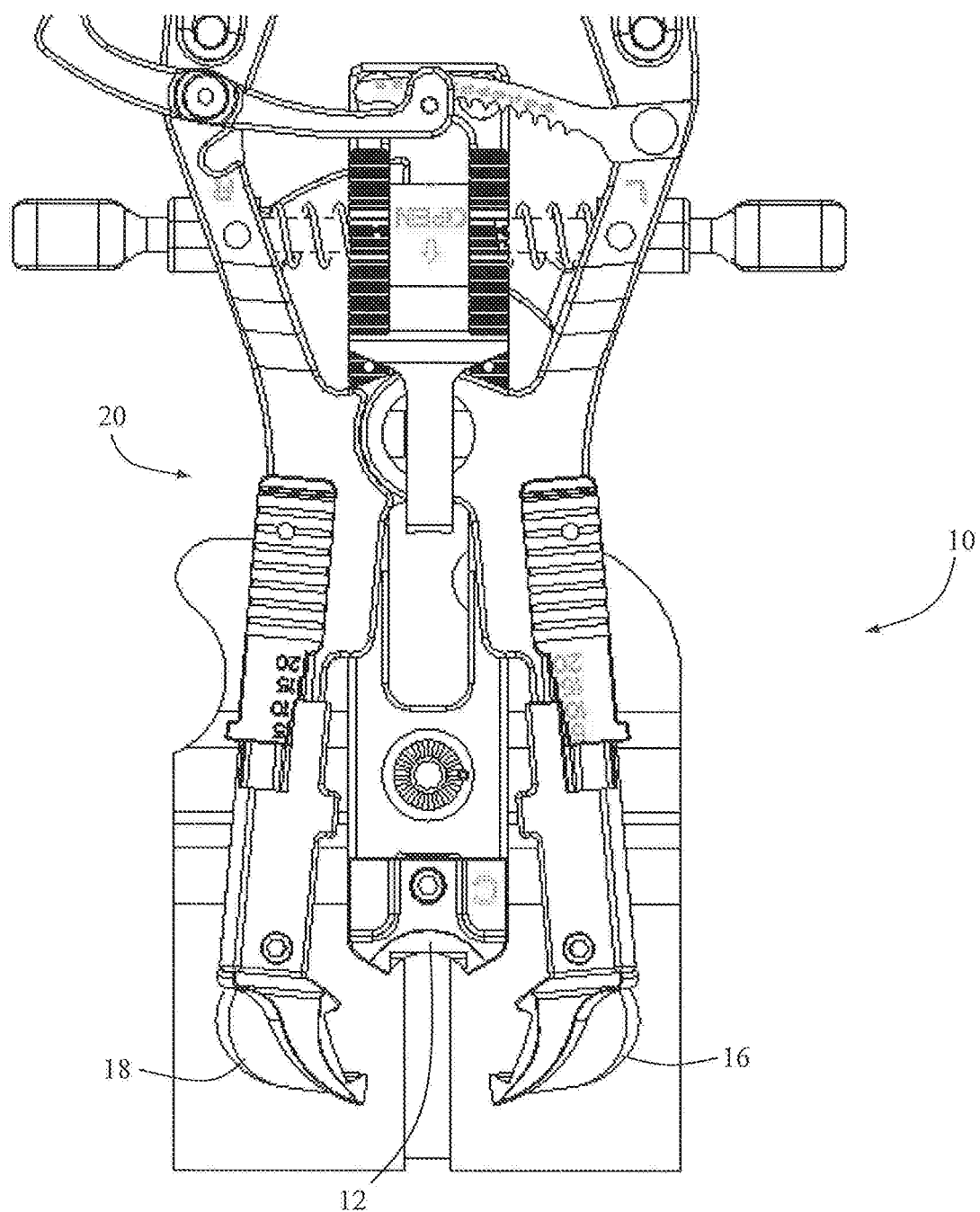
Figure 51:
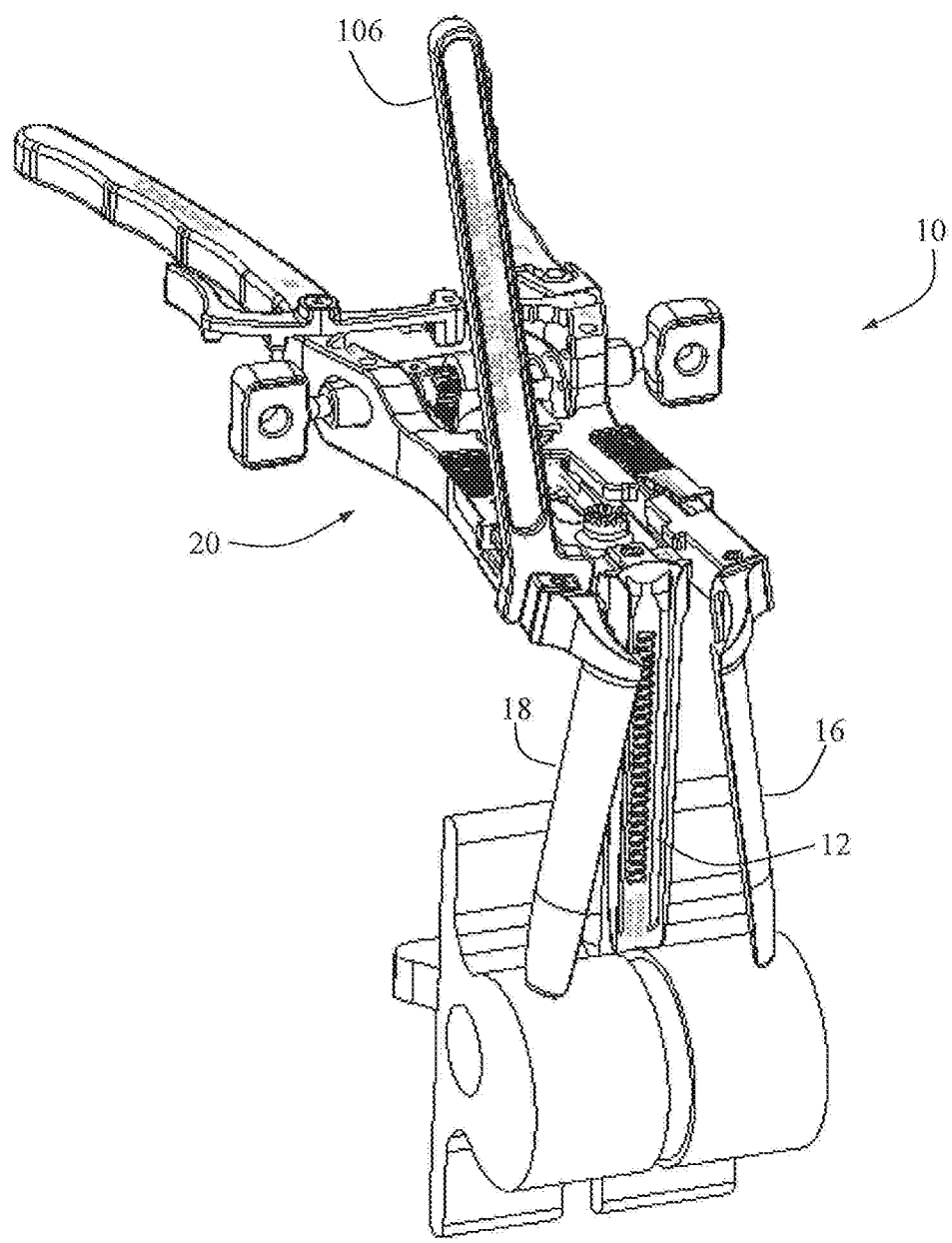
FIGS. 51-52 are perspective views of the retractor assembly of FIG. 50 with the retractor arms in a pivoted position.
Figure 52:
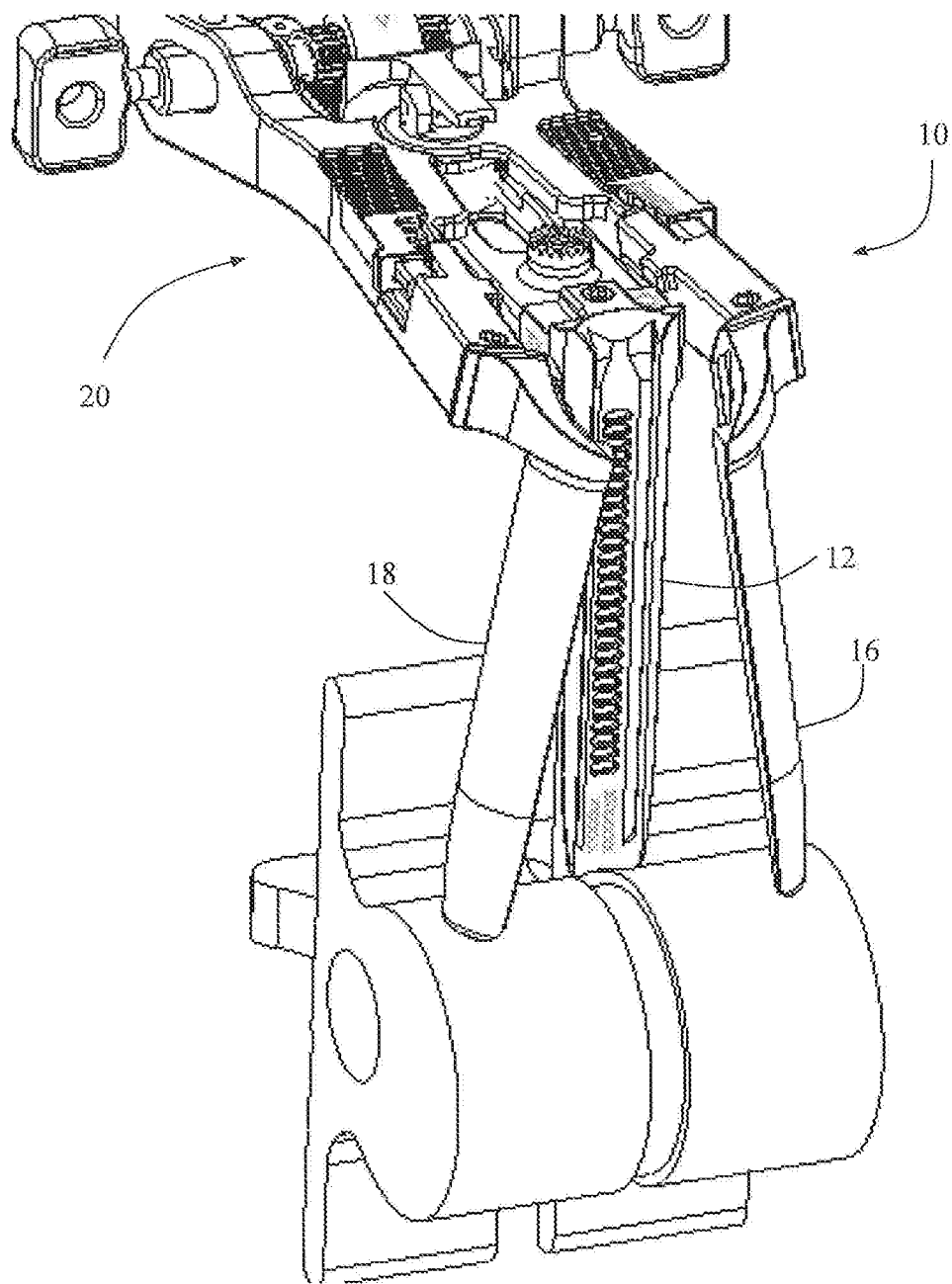
Figure 53:
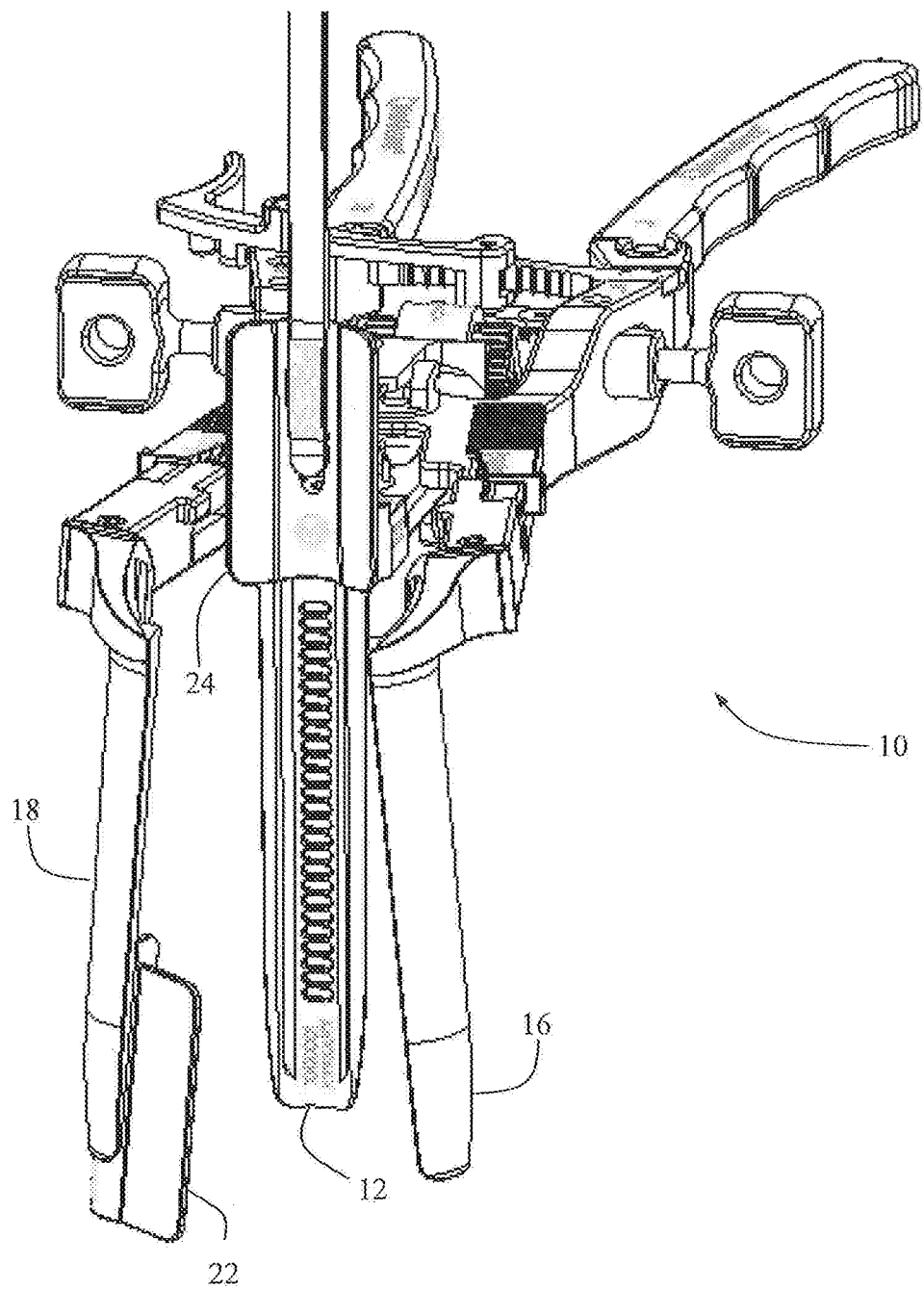
FIG. 53 is a perspective view of the retractor assembly in the second, opened (i.e. retracted) position (with the secondary distraction assembly removed) and with one retractor extender of FIGS. 6-7 coupled to a retractor blade and another retractor being inserted onto a second retractor blade according to the present invention.

As shown in FIG. 47, the retraction assembly 10 of the present invention is thereafter advanced along the exterior of the sequential dilation system 50. This is accomplished by maintaining the retractor blades 12, 16, 18 in a first, closed position (with the retractor blades 12-16 in generally abutting relation to one another as shown in FIGS. 2-3). Once advanced to the surgical target site, the sequential dilation assembly 50 may be removed and the shim element 25 engaged with the first retractor blade 12 such that the distal end thereof extends into the disc space as shown in FIG. 48. At this point, the handle assembly 20 may be operated to move the retractor blades 16, 18 into a second, "retracted" position as shown generally in FIGS. 49-50. As will be appreciated; the first retractor blade 12 is allowed to stay in the same general position during this process, such that the second and third retractor blades 16, 18 move away from the first retractor blade 12. Optionally, the second retractor blade 16 and/or the/third retractor blade 18 may be pivoted in an outward direction as shown in FIGS. 51-52. At this point, the narrow and wide retractor extenders 22, 24, 60 may be engaged with any combination of retractor blades 12, 16, 18 as described above and as shown in FIG. 53.

Figure 54:
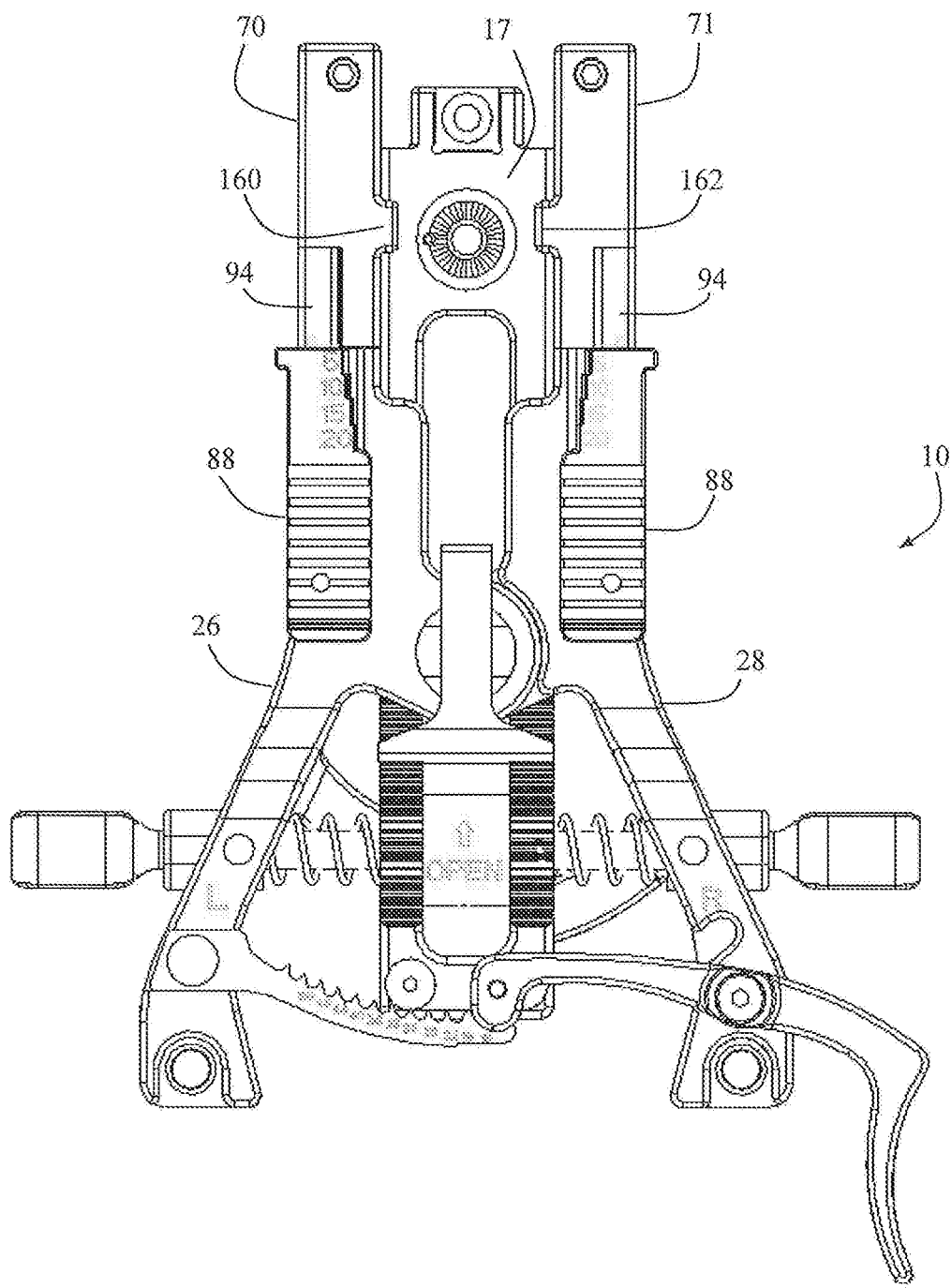
FIGS. 54-55 are perspective views of a handle assembly forming part of the tissue retraction assembly of FIG. 1 shown in an initial closed position.
Figure 55:
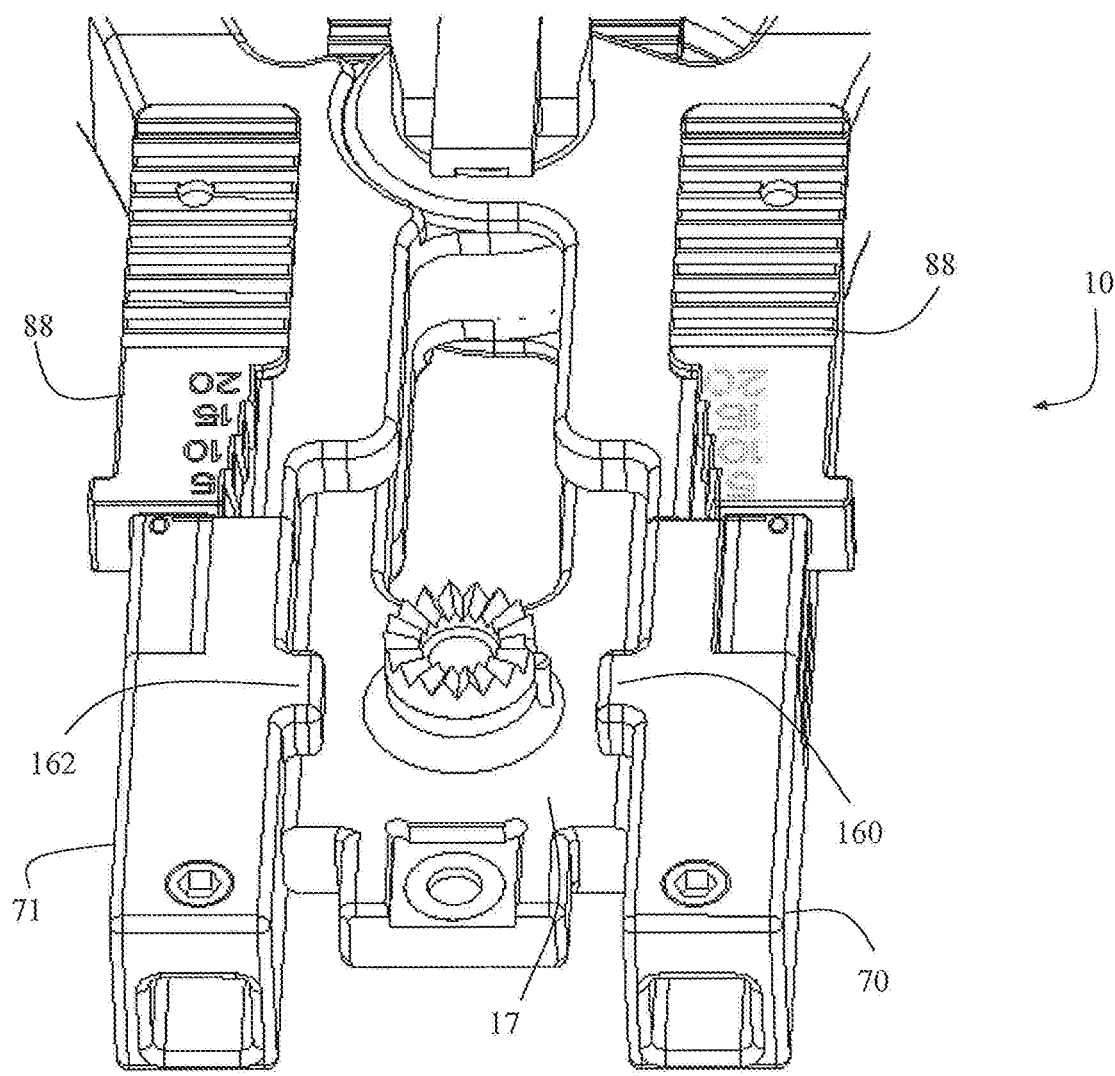

Various improvements and modifications may be made to the surgical access system disclosed herein without deviating from the scope of the present invention. For example, as exemplified in FIGS. 54-56, the tissue retraction system 10 may include an optional locking feature to maintain the blades 16, 18 in an initial alignment (e.g. generally parallel) during insertion. By way of example only, this locking feature may consist of a pair of tabs 160, 162 located on the distal pivot member 70, 71 of first and second arm members 26, 28, respectively. The tabs 160, 162 are dimensioned to extend at least partially over the translating member 17 such that when the tissue retraction system 10 is in an initial closed position as shown in FIGS. 54-55 (e.g. as the tissue retraction system 10 is advanced along the exterior of sequential dilation system 50), the distal pivot members 70, 71 are prevented from pivoting, thereby maintaining the retractor blades 16, 18 in an initial alignment.

Figure 24:
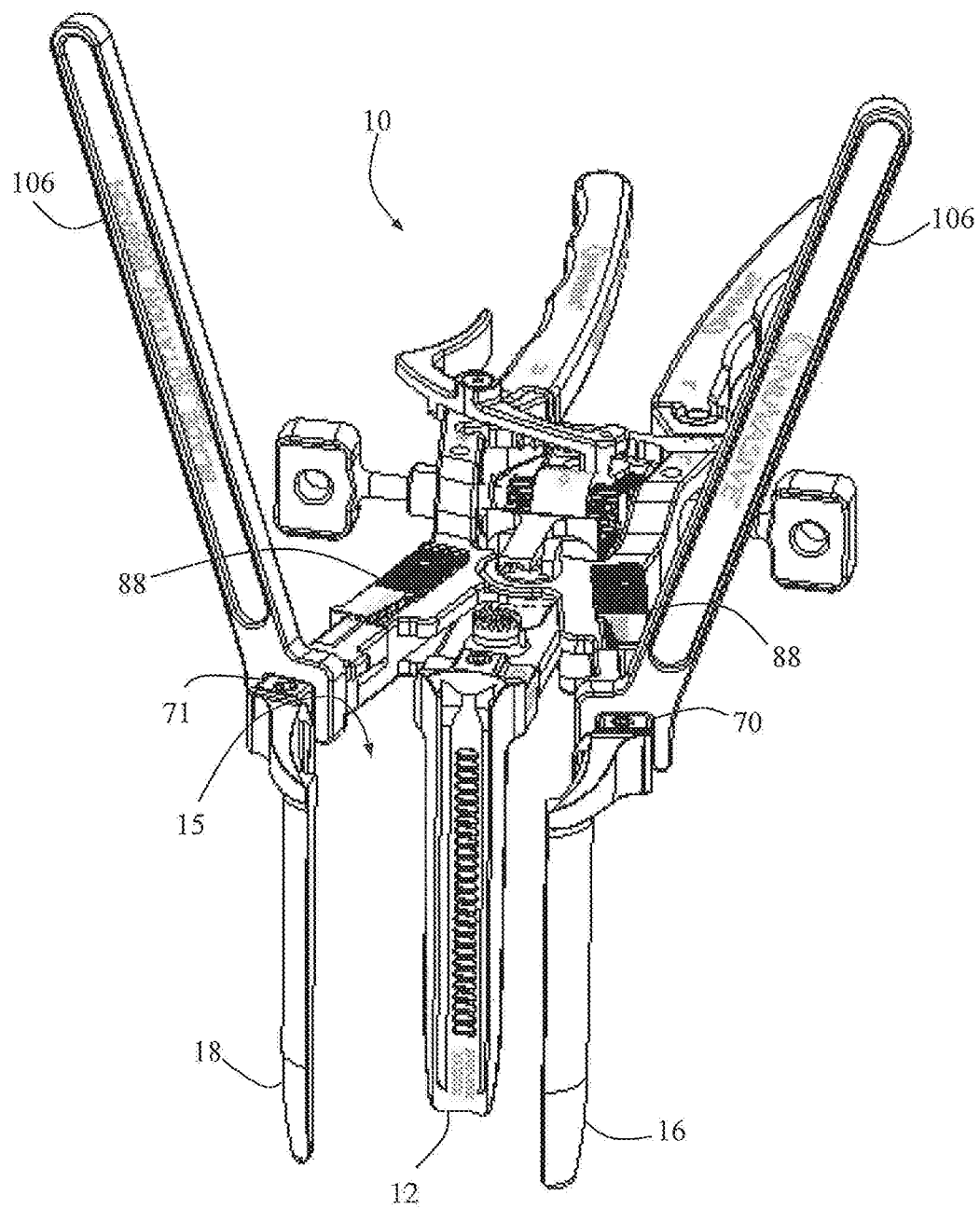
FIG. 24 is a perspective view of the tissue retraction assembly of FIG. 1 in conjunction with a pair of pivot wrenches before the blades have been pivoted.
Figure 56:
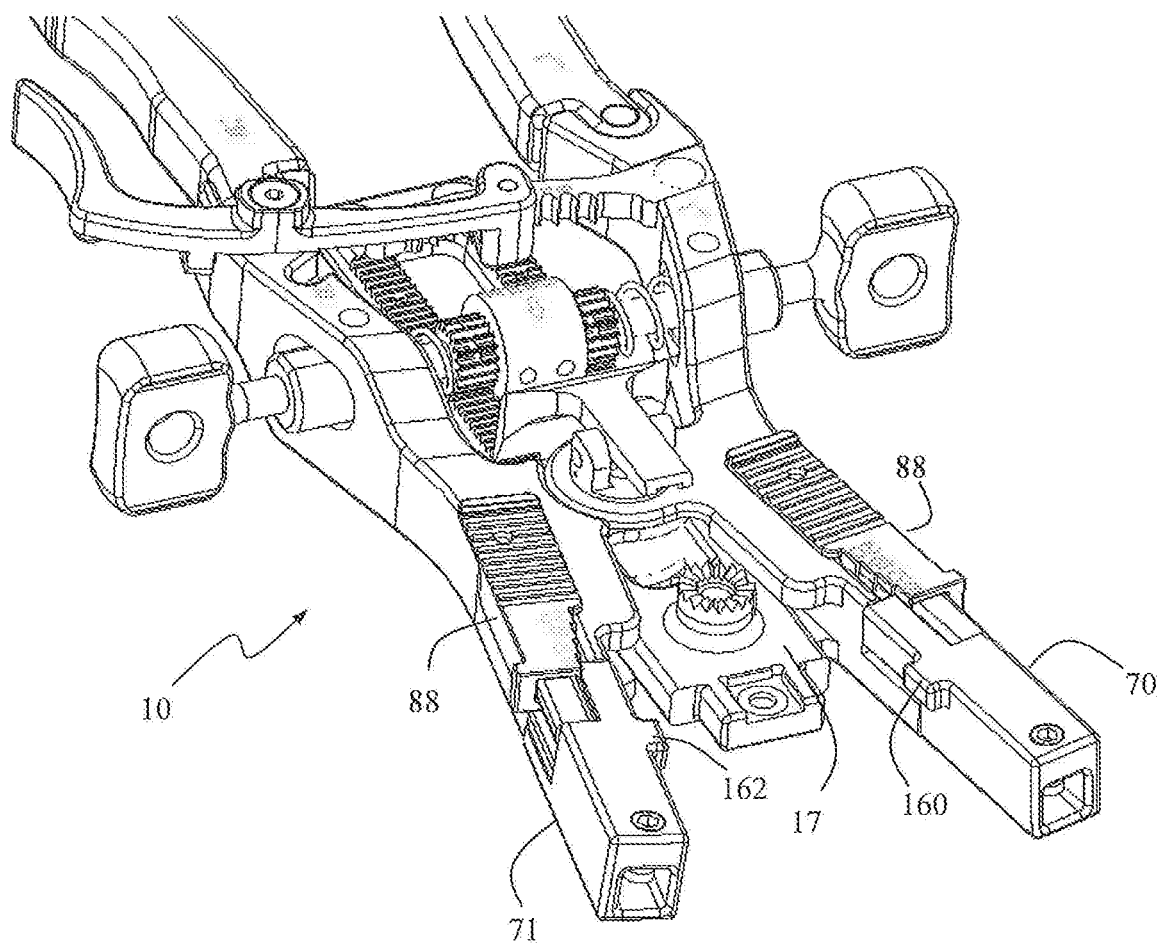
FIG. 56 is a perspective view of the handle assembly of FIG. 54 shown in a secondary open position.

Once the tissue retraction system 10 is fully in place and the sequential dilation system 50 has been removed as described above, the handle assembly 20 may be operated to move the first and second arm members 26, 28 into a second position shown generally in FIG. 56. In so doing, retractor blades 16, 18 are also moved into a second, "retracted" position. The presence of the patient's soft tissue defining the walls of the operative corridor is generally sufficient to maintain the retractor blades 16, 18 in the initial (e.g. generally vertical) alignment despite the fact that locking tabs 160, 162 are no longer engaged with translating member 17. At this point, the surgeon may elect to expand the operative corridor IS by manually pivoting the retractor blades 16, 18 in a generally outward direction, using by way of example only either a pivot wrench 106 (FIGS. 24-26) and/or a blade expander 112 (FIGS. 31-33) as described above.

As mentioned above, any number of distraction components and/or retraction components (including but not limited to those described herein) may be equipped to detect the presence of (and optionally the distance and/or direction to) neural structures during tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist). Such monitoring may also be carried out via the surgeon-driven EMG monitoring system shown and described in the commonly owned and co-pending NeuroVision PCT Applications referenced above. In any case (visual monitoring, traditional EMO and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 57:
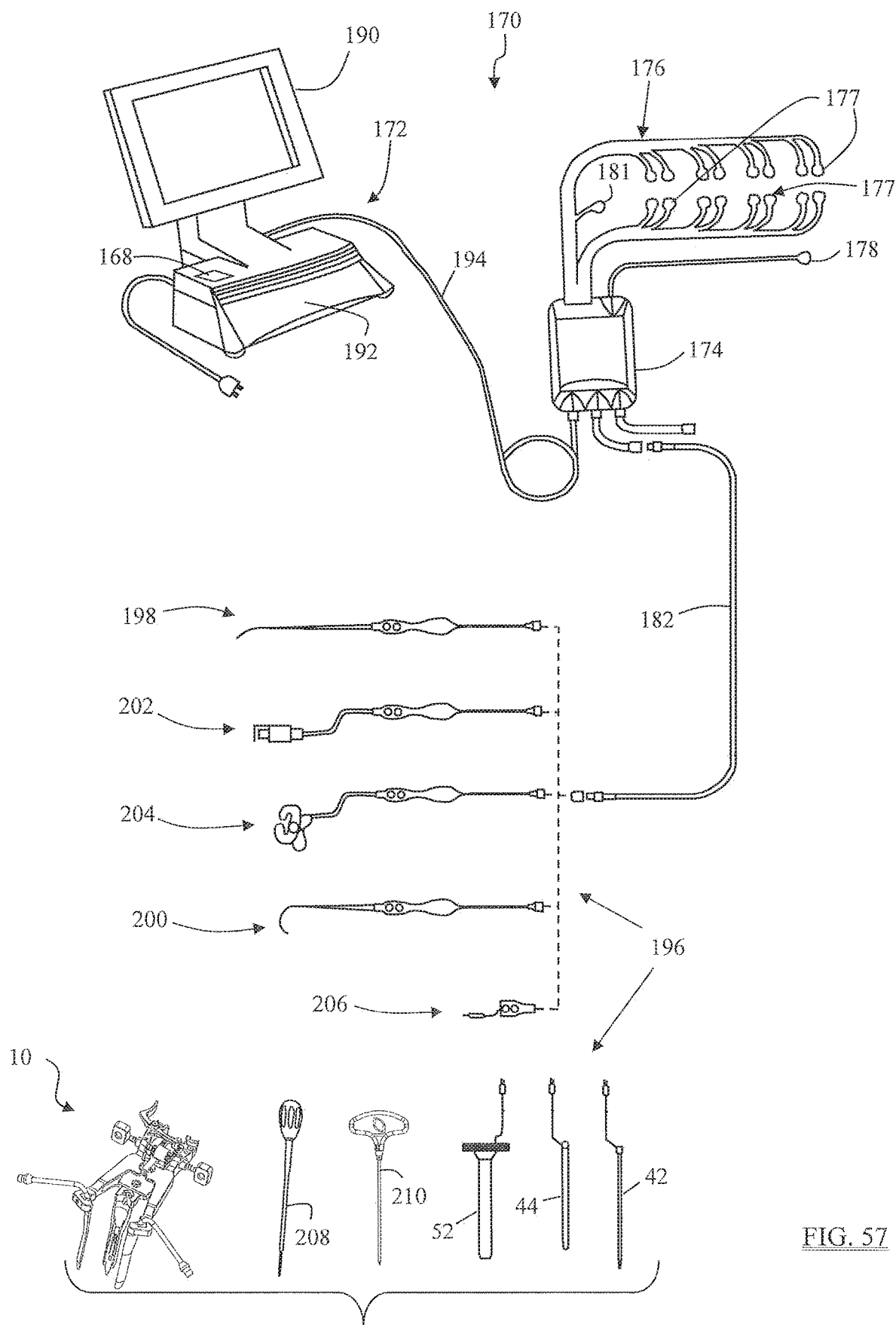
FIG. 57 is a perspective view of an exemplary nerve monitoring system capable of performing nerve monitoring before, during and after the creating of an operative corridor to a surgical target site using the surgical access system in accordance with the present invention.
Figure 58:
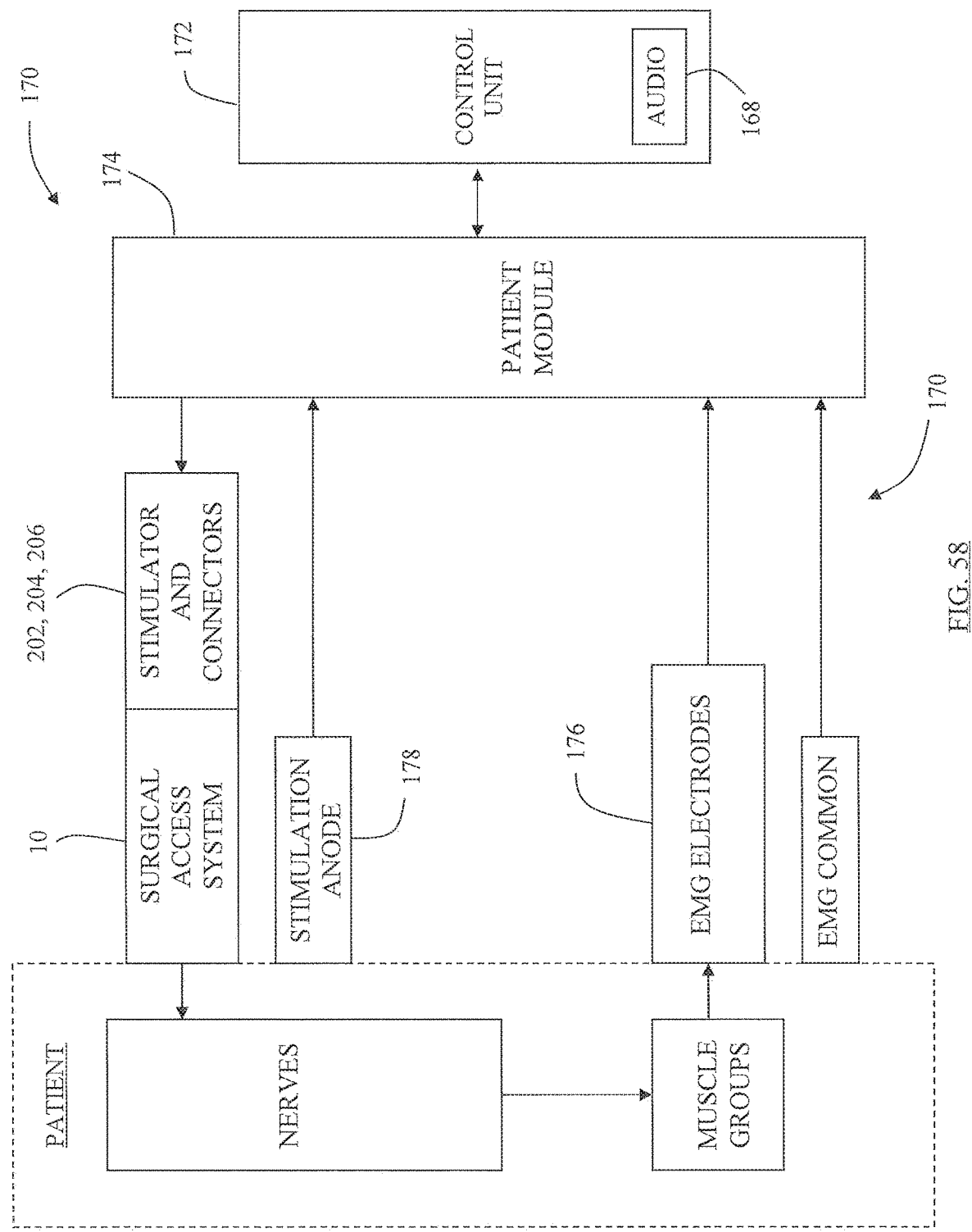
FIG. 58 is a block diagram of the nerve monitoring system shown in FIG. 57.

FIGS. 57-58 illustrate, by way of example only, a monitoring system 170 of the type disclosed in the NeuroVision PCT Applications suitable for use with the surgical access system 10 of the present invention. The monitoring system 170 includes a control unit 172, a patient module 174, and an EMG harness 176 and return electrode 178 coupled to the patient module 174, and a cable 182 for establishing electrical communication between the patient module 174 and any number of surgical accessories 196, including the surgical access system of the present invention (retractor assembly 10 of FIG. 1 and distraction assemblies 40, 50 of FIGS. 46-47, including K-wire 42, initial dilator 44 and sequentially dilating cannulae 52, 54). The surgical accessories 196 may further include, but are not necessarily limited to, devices for performing pedicle screw tests (such as a screw test probe 198), neural pathology monitoring devices (such as a nerve root retractor 200), coupling devices for electronically coupling surgical instruments to the system 170 (such as electric coupling devices 202, 204 and stimulator driver 206), and pilot hole forming components (such as a tap member 208, pedicle access probe 210, or other similar device). More specifically, this electrical communication can be achieved by providing, by way of example only, a hand-held stimulation driver 206 capable of selectively providing a stimulation signal (due to the operation of manually operated buttons on the hand-held stimulation controller 206) to one or more connectors (e.g., coupling devices 202, 204). The coupling devices 202, 204 are suitable to establish electrical communication between the hand-held stimulation controller 206 and (by way of example only) the stimulation electrodes on the K-wire 42, the dilators 44, 52, 54, the retractor blades 12, 16, 18 and/or the shim members 22, 24, 25, 60 (collectively "surgical access instruments").

In order to use the monitoring system 170, then, these surgical access instruments must be connected to at least one of coupling devices 202, 204 (or their equivalent), at which point the user may selectively initiate a stimulation signal (preferably, a current signal) from the control unit 172 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 172 includes a touch screen display 190 and a base 192, which collectively contain the essential processing capabilities (software and/or hardware) for controlling the monitoring system 170. The control unit 172 may include an audio unit 168 that emits sounds according to a location of a surgical element with respect to a nerve. The patient module 174 is connected to the control unit 172 via a data cable 194, which establishes the electrical connections and communications (digital and/or analog) between the control unit 172 and patient module 174. The main functions of the control unit 172 include receiving user commands via the touch screen display 190, activating stimulation electrodes on the surgical access instruments, processing signal data according to defined algorithms, displaying received parameters and processed data, and monitoring system status and report fault conditions. The touch screen display 190 is preferably equipped with a graphical user interface (GUI) capable of communicating information to the user and receiving instructions from the user. The display 190 and/or base 192 may contain patient module interface circuitry (hardware and/or software) that commands the stimulation sources, receives digitized signals and other information from the patient module 174, processes the EMG responses to extract characteristic information for each muscle group, and displays the processed data to the operator via the display 190.

In one embodiment, the monitoring system 170 is capable of determining nerve direction relative to one or more of the K-wire 42, the dilators 44, 52, 54, the retractor blades 12, 16, 18 and/or the shim elements 22, 24, 25, 60 before, during and/or following the creation of an operative corridor to a surgical target site. Monitoring system 170 accomplishes this by having the control unit 172 and patient module 174 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 176. The nerve direction feature of the system 170 is based on assessing the evoked response of the various muscle myotomes monitored by the system 170 via the EMG harness 176.

By monitoring the myotomes associated with the nerves (via the EMG harness 176 and recording electrode 177) and assessing the resulting EMG responses (via the control unit 172), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

Figure 59:
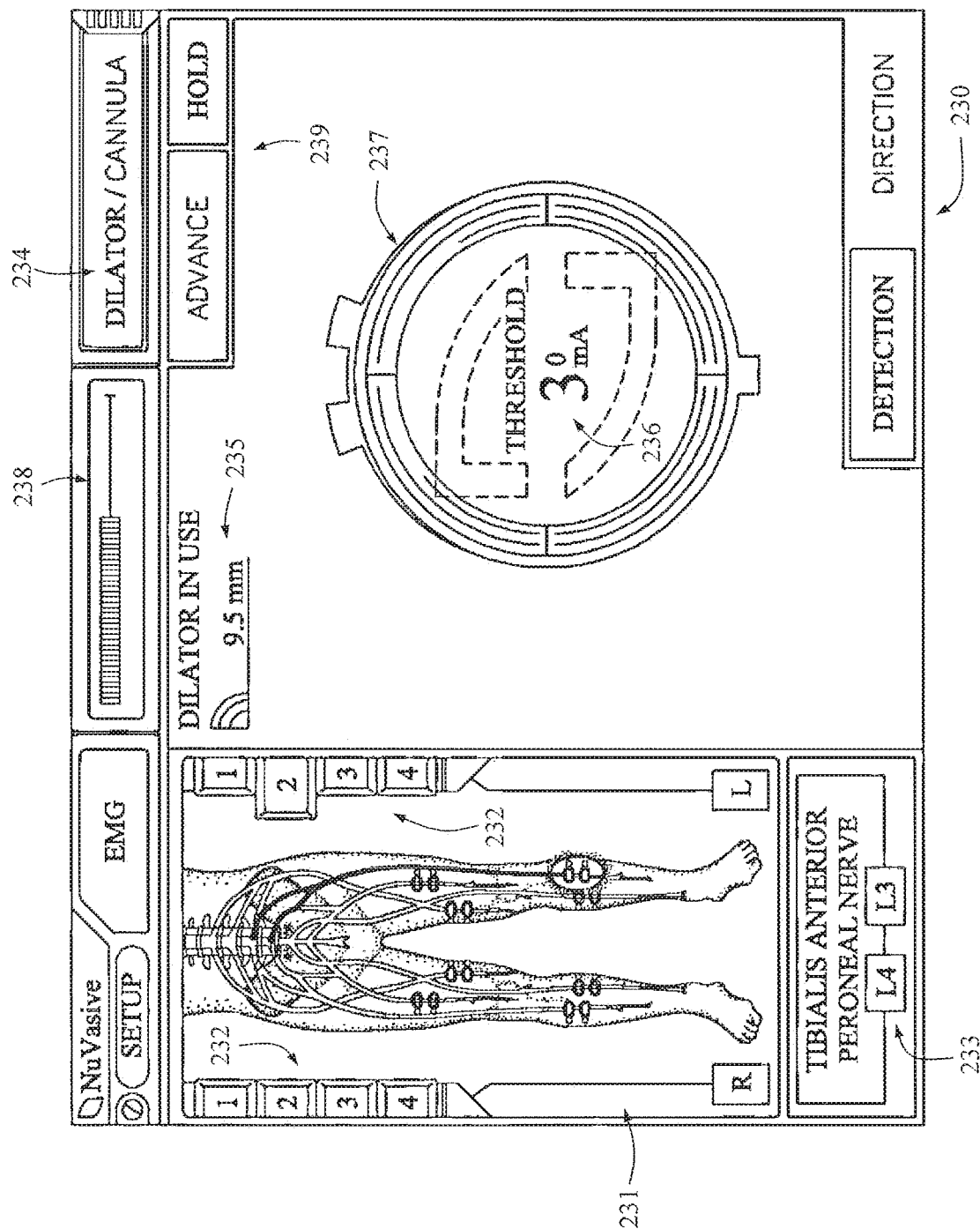
FIGS. 59-60 are screen displays illustrating exemplary features and information communicated to a user during the use of the nerve monitoring system of FIG. 57.
Figure 60:
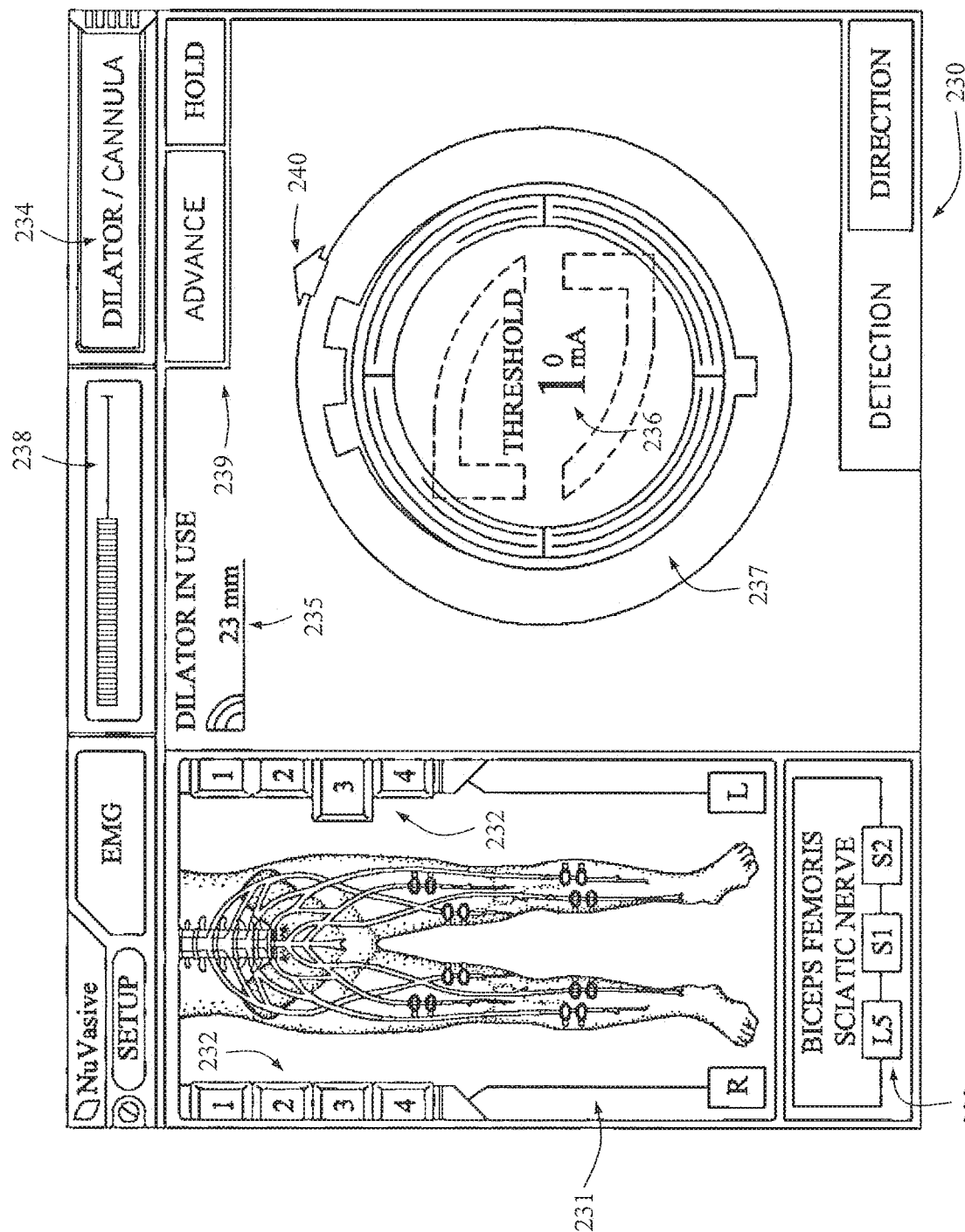

FIGS. 59-60 are exemplary screen displays (to be shown on the display 190) illustrating one embodiment of the nerve direction feature of the monitoring system shown and described with reference to FIGS. 57-58. These screen displays are intended to communicate a variety of information to the surgeon in an easy-to-interpret fashion. This information may include, but is not necessarily limited to, a display of the function 230 (in this case "DIRECTION"), a graphical representation of a patient 231, the myotome levels being monitored 232, the nerve or group associated with a displayed myotome 233, the name of the instrument being used 234 (in this case, a dilator 52, 54), the size of the instrument being used 235, the stimulation threshold current 236, a graphical representation of the instrument being used 237 (in this case, a cross-sectional view of a dilator 52, 54) to provide a reference point from which to illustrate relative direction of the instrument to the nerve, the stimulation current being applied to the stimulation electrodes 238, instructions for the user 239 (in this case, "ADVANCE" and/or "HOLD"), and (in FIG. 60) an arrow 240 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 234), it is to be readily appreciated that the present invention is deemed to include providing similar information on the display 190 during the use of any or all of the various instruments forming the surgical access system 10 of the present invention, including the distraction assembly 40 (i.e. the K-wire 42 and dilators 44, 52, 54) and/or the retractor blades 12, 16, 18 and/or the shim elements 22, 24, 25, 60.

As evident from the above discussion and drawings, the present invention accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present invention furthermore provides the ability to perform neural monitoring in the tissue or regions adjacent the surgical target site during any procedures performed after the operative corridor has been established. The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PLIF, ALIF, TLIF and any fusion effectuated via a lateral or far-lateral approach and involving, by way of example, the introduction and/or removal of bone products (such as allograft or autograft) and/or devices having ceramic, metal and/or plastic construction (such as mesh) and/or compounds such as bone morphogenic protein), total disc replacement, etc. . . . ).

Moreover, the surgical access system of the present invention opens the possibility of accessing an increased number of surgical target sites in a "less invasive" fashion by eliminating or greatly reducing the threat of contacting nerves or neural structures while establishing an operative corridor through or near tissues containing such nerves or neural structures. In so doing, the surgical access system of the present invention represents a significant advancement capable of improving patient care (via reduced pain due to "less-invasive" access and reduced or eliminated risk of neural contact before, during, and after the establishment of the operative corridor) and lowering health care costs (via reduced hospitalization based on "less-invasive" access and increased number of suitable surgical target sites based on neural monitoring). Collectively, these translate into major improvements to the overall standard of care available to the patient population, both domestically and overseas.

What is claimed is:

1. A method of accessing a surgical target site, the method comprising:
introducing a retractor assembly comprising three blades to the surgical target site along a longitudinal axis while the three blades are in a closed position in which each of the three blades abuts the other two blades, wherein at least one of the three blades is pivotally coupled to a handle assembly and configured to pivot about a pivot axis orthogonal to the longitudinal axis, two or more of the three blades are arcuate in cross-section, and one of the three blades is a posterior blade rigidly coupled to a translating member coupled to the handle assembly via a linkage assembly comprising a roller member, the linkage assembly configured to move the translating member in a linear fashion with respect to the handle assembly; and
adjusting the plurality of blades of the retractor assembly at the surgical target site to an opened position to create an operative corridor with the plurality of blades, wherein adjusting the plurality of blades to the opened position to create the operative corridor comprises:
rotating the roller member of the retractor assembly in a first rotational direction to drive the translating member and posterior blade away from the handle assembly without moving the other blades with respect to the handle assembly.

2. The method of claim 1, wherein adjusting the plurality of blades to the opened position to create the operative corridor comprises rotating the roller member in a second rotational direction to linearly translate the translating member and posterior blade toward the handle assembly without moving the other blades with respect to the handle assembly.

3. The method of claim 1, wherein linear translation of the first blade is performed independent of moving the other blades of the plurality of blades.

4. The method of claim 1, wherein adjusting the retractor assembly at the surgical target site to create the operative corridor comprises:
pivoting one or both of a second blade of the plurality of blades and a third blade of the plurality of blades away from a central axis along which the retractor assembly is introduced to the surgical target site.

5. The method of claim 4, wherein the first blade is a posterior blade, the second blade is a cephalad blade, and the third blade is a caudal blade.

6. The method of claim 1, further comprising:
creating a distraction corridor to the surgical target site with a distraction assembly prior to introducing the retractor assembly to the surgical target site.

7. The method of claim 6, wherein creating the distraction corridor comprises:
inserting a K-wire to the surgical target site; and
sliding a dilator over the K-wire to the surgical target site.

8. The method of claim 7, wherein the K-wire includes a stimulation electrode at a distal tip of the K-wire and the method further comprises:
emitting an electrical stimulation signal from the stimulation electrode; and
determining if the electrical stimulation signal causes muscles associates with neural structures around the surgical target site to innervate.

9. The method of claim 6, wherein introducing the retractor assembly to the surgical target site includes advancing the plurality of blades through the distraction corridor to the surgical target site.

10. The method of claim 6, further comprising:
removing the distraction assembly prior to adjusting one or both of the second blade and the third blade radially outward from the first blade to the first position.

11. The method of claim 1, further comprising:
emitting an electrical stimulation signal proximate the surgical target site; and
determining if the electrical stimulation signal causes muscles associates with neural structures around the surgical target site to innervate.

12. The method of claim 1, comprising:
rotating one or both of the second blade and the third blade to a second position at which a distance between distal ends of the second blade and the third blade is greater than the distance between the distal ends of the second blade and the third blade in the first position.

* * * * *